United States Patent
Corey et al.

(10) Patent No.: US 10,934,331 B2
(45) Date of Patent: Mar. 2, 2021

(54) METHODS FOR ENHANCING IMMUNE RESPONSIVENESS IN AN INDIVIDUAL TOWARD A TARGET CANCER CELL POPULATION COMPRISING APOPTOTIC CELLS

(71) Applicant: The Board of Trustees of the Leland Stanford Junior University, Stanford, CA (US)

(72) Inventors: Daniel Mark Corey, Palo Alto, CA (US); Aaron Michael Ring, New Haven, CT (US); Melissa N. McCracken, Boston, MA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/324,240

(22) PCT Filed: Aug. 4, 2017

(86) PCT No.: PCT/US2017/045577
§ 371 (c)(1),
(2) Date: Feb. 8, 2019

(87) PCT Pub. No.: WO2018/031419
PCT Pub. Date: Feb. 15, 2018

(65) Prior Publication Data
US 2019/0218260 A1 Jul. 18, 2019

Related U.S. Application Data

(60) Provisional application No. 62/374,477, filed on Aug. 12, 2016.

(51) Int. Cl.
| | |
|---|---|
| *A61K 35/17* | (2015.01) |
| *A61K 38/17* | (2006.01) |
| *A61K 45/06* | (2006.01) |
| *C07K 14/47* | (2006.01) |
| *C07K 14/00* | (2006.01) |
| *C07K 14/435* | (2006.01) |
| *C07K 14/62* | (2006.01) |
| *C12N 15/86* | (2006.01) |

(52) U.S. Cl.
CPC .............. *C07K 14/47* (2013.01); *A61K 35/17* (2013.01); *A61K 38/1709* (2013.01); *A61K 45/06* (2013.01); *C07K 14/00* (2013.01); *C07K 14/435* (2013.01); *C07K 14/62* (2013.01); *C12N 15/86* (2013.01); *C07K 2319/30* (2013.01); *C12N 2740/13043* (2013.01)

(58) Field of Classification Search
CPC ...... C07K 14/00; C07K 14/435; C07K 14/47; C07K 14/62; C07K 2319/30; C12N 15/86; C12N 2740/13043; A61K 45/06; A61K 38/1709; A61K 35/17
See application file for complete search history.

(56) References Cited

U.S. PATENT DOCUMENTS

2015/0297677 A1 10/2015 Choe et al.
2016/0060358 A1 3/2016 Hay

OTHER PUBLICATIONS

Carnec et al. "The Phosphatidylserine and Phosphatidylethanolamine Receptor CD300a Binds Dengue Virus and Enhances Infection," J Virol., Oct. 14, 2015, pp. 92-102, vol. 90, Iss. 1, American Society of Microbiology, Washington, DC.
Kobayashi et al. "T cell immunoglobulin Mucin Protein (TIM)-4 binds phosphatidylserine and mediates uptake of apoptotic cells", Immunity, Dec. 21, 2007, pp. 927-940, vol. 27, Iss. 6, Elsevier, New York City, NY.
Miyanishi et al. "Identification of Tim4 as a phosphatidylserine receptor," Nature, Nov. 15, 2007, pp. 435-439, vol. 450, Springer Publishing, New York City, NY.

*Primary Examiner* — Robert S Landsman
(74) *Attorney, Agent, or Firm* — Pamela J. Sherwood; Bozicevic, Field & Francis LLP

(57) ABSTRACT

Cell loss by apoptosis is a common feature in certain conditions, including cancer. Dying tumor cells induce immune tolerance within the tumor microenvironment largely through highly conserved homeostatic clearance programs that are designed to restore tissue homeostasis and contribute to the formation of an immunosuppressive niche. The translocation of phosphatidylserine (PS) on cellular membranes, during the initial phases of apoptosis, functions as a recognition and removal signal that limits the immunogenicity of cell death. To remove inhibitory signals in the homeostatic clearance pathway a fusion protein comprising a phosphatidylserine binding domain and an immunostimulatory domain can restore immune responses to dead tumor cells in antigen cross presentation assays and promotes recruitment and retention of tumor antigen specific immune effector cells into tumors. These effects combine to elicit anti-tumor immunity, improve responses to immune checkpoint inhibitors, and enhance the effectiveness of adoptive T cell transfers using engineered T cells.

11 Claims, 13 Drawing Sheets
Specification includes a Sequence Listing.

Modified bridge protein

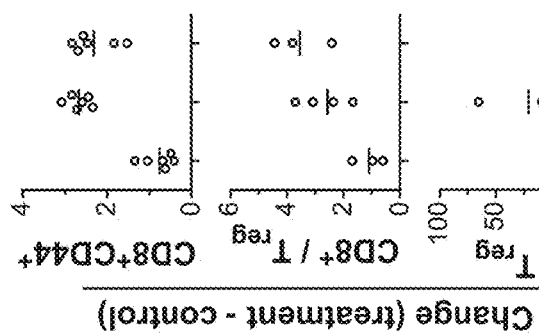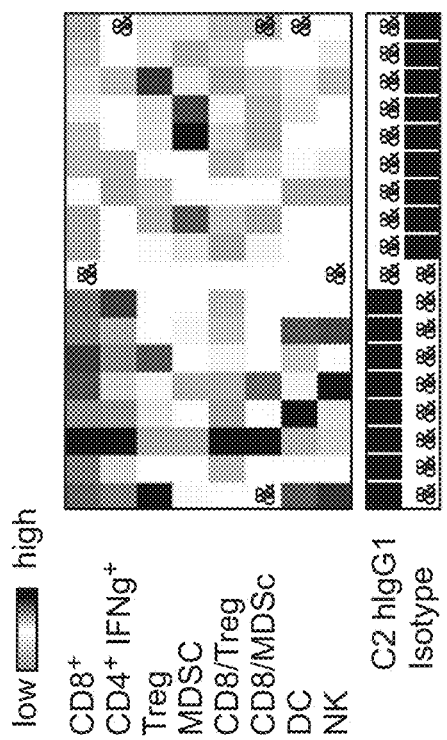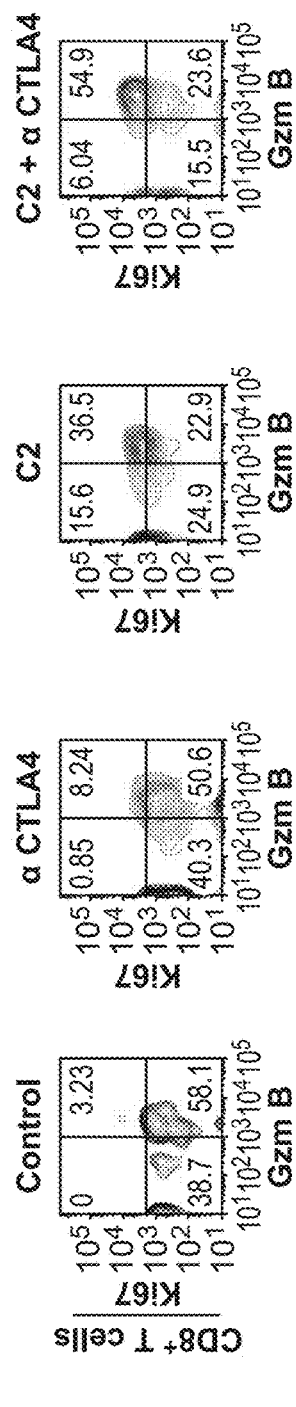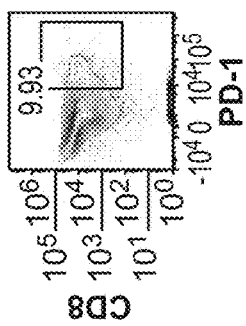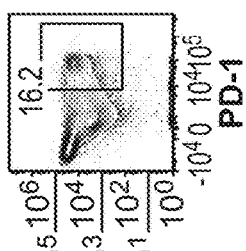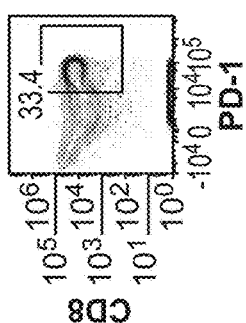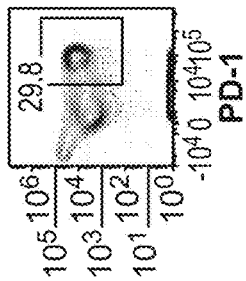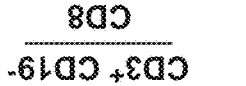

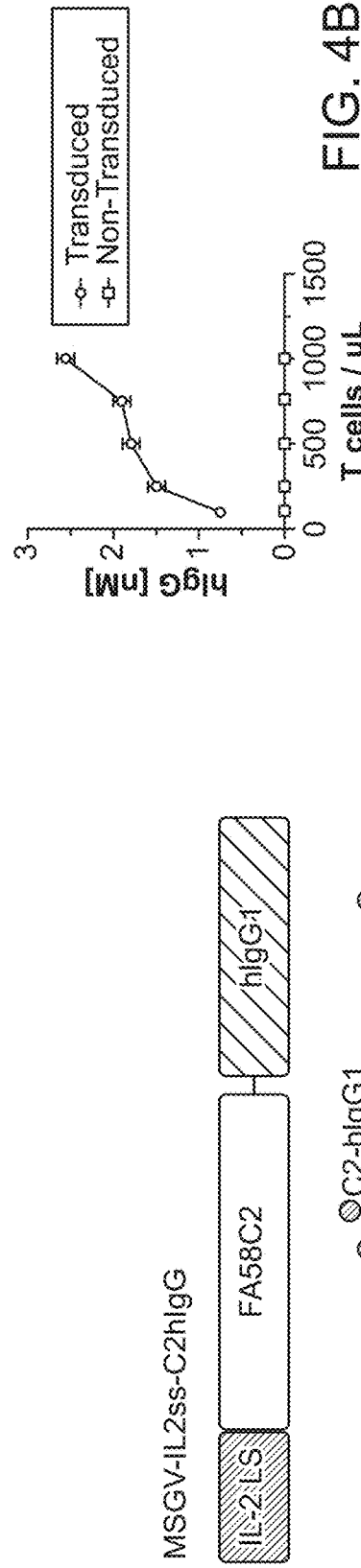
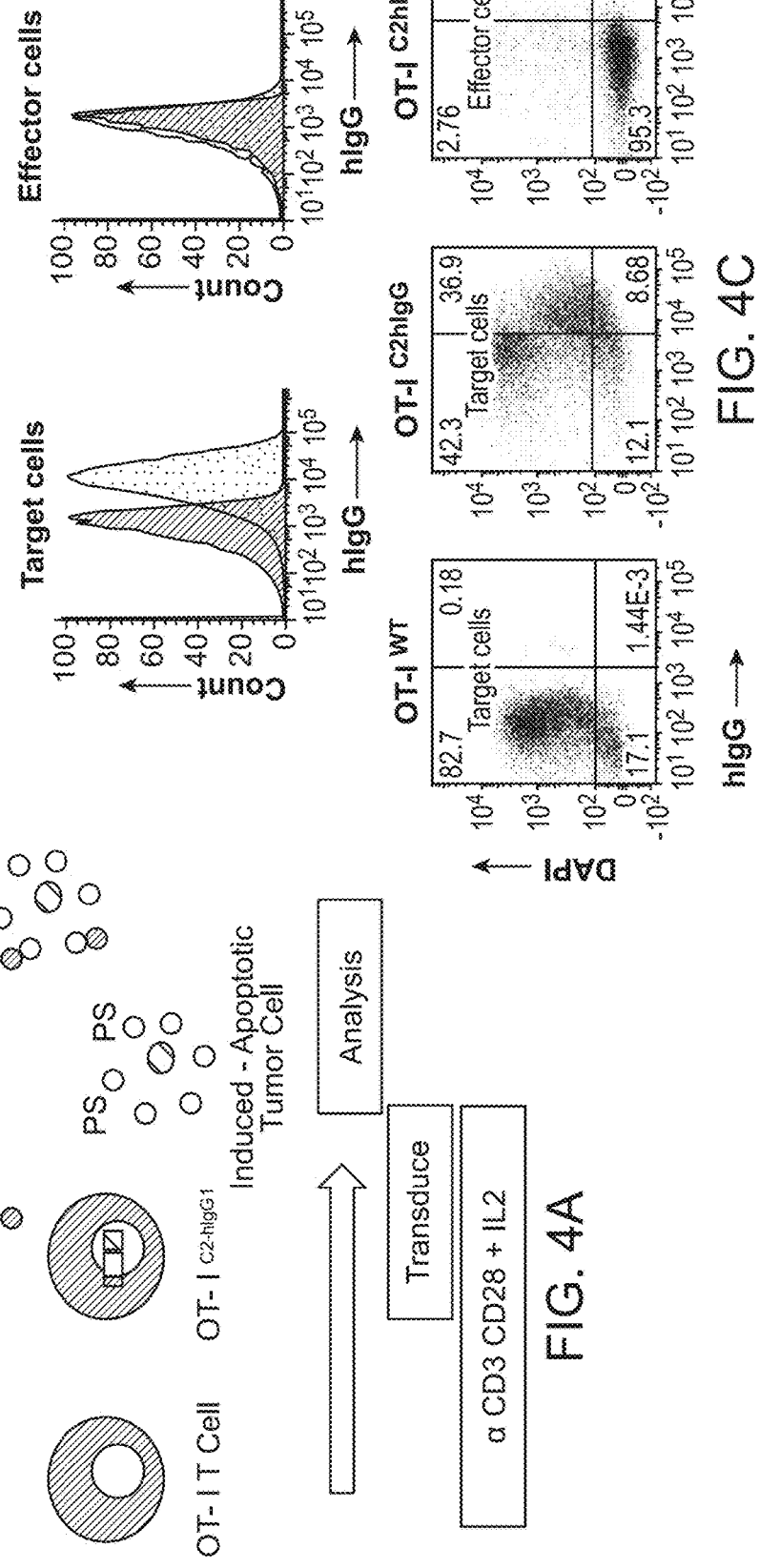
FIG. 4A
FIG. 4B
FIG. 4C

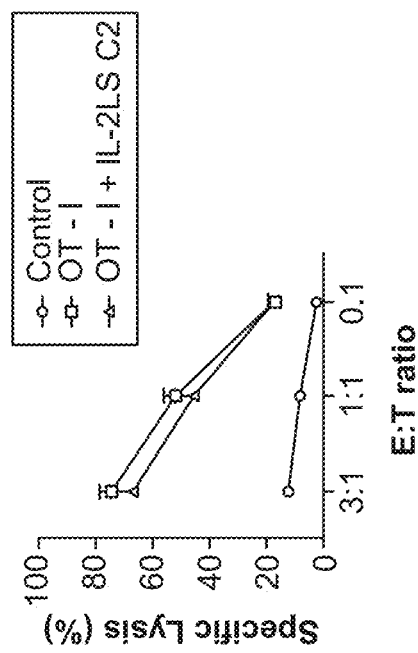
FIG. 4D
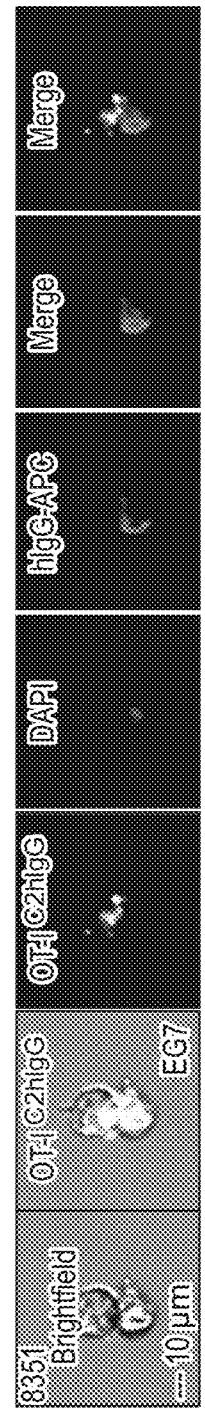
FIG. 4E
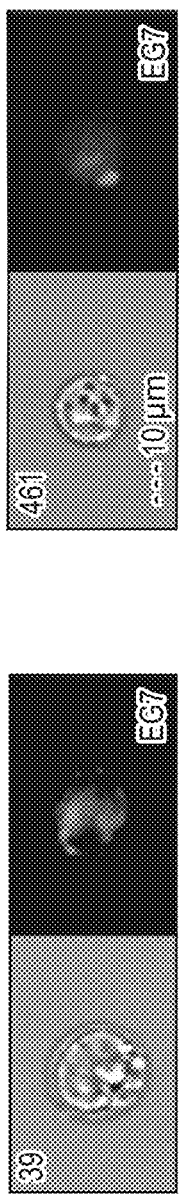
FIG. 4F
FIG. 4G

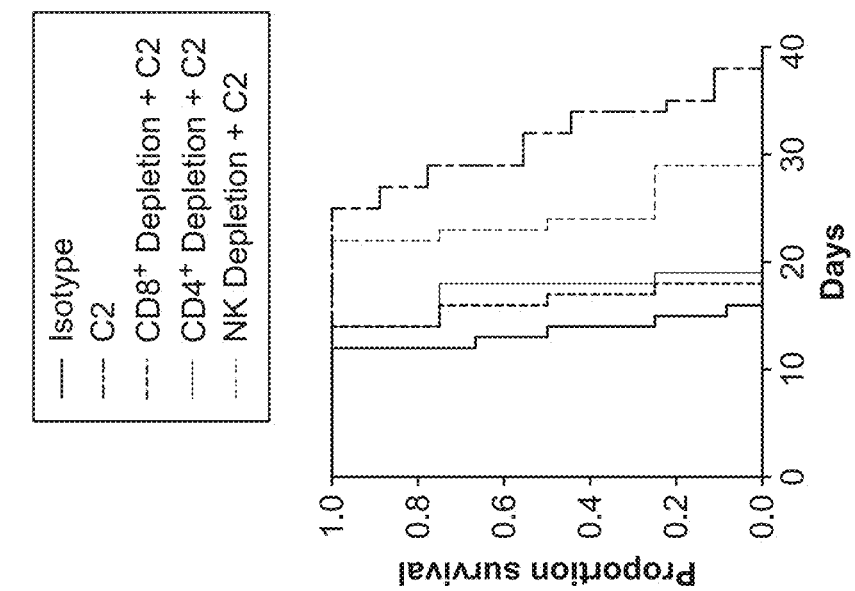
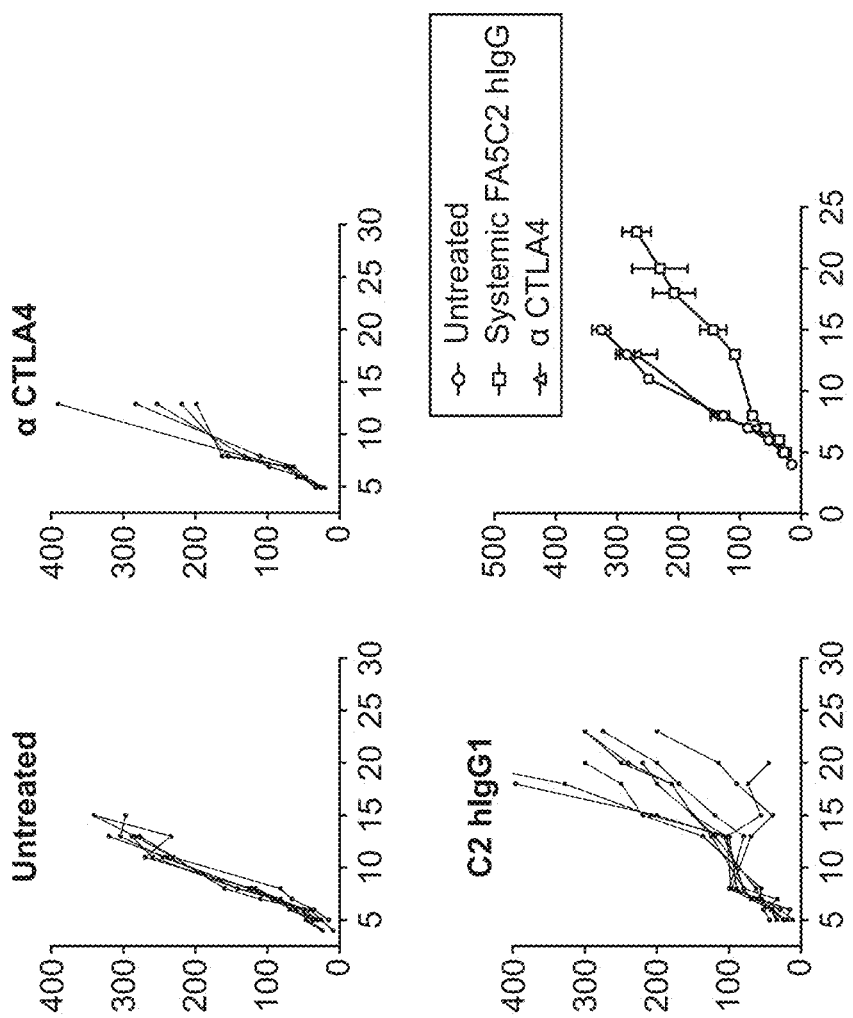
FIG. 7A
FIG. 7B

METHODS FOR ENHANCING IMMUNE RESPONSIVENESS IN AN INDIVIDUAL TOWARD A TARGET CANCER CELL POPULATION COMPRISING APOPTOTIC CELLS

CROSS REFERENCE

This application claims benefit of and is a 371 application of PCT Application No. PCT/US2017/045577, filed Aug. 4, 2017, which claims benefit of U.S. Provisional Patent Application No. 62/374,477, filed Aug. 12, 2016, which applications are incorporated herein by reference in their entirety.

BACKGROUND OF THE INVENTION

Cross presentation is the process of production of peptide-MHC Class I complexes by cells in which the antigen that is the source of peptide is not translated. During normal development and tissue turnover, cells are programmed to undergo apoptosis and cell corpses are subsequently removed by professional phagocytes (macrophages) or neighboring cells. The recognition and engulfment of apoptotic cell corpses is thought to prevent chronic inflammation through the disposal of dying cells prior to the leakage from these cells of noxious constituents into surrounding tissues. Moreover, rapid engulfment of apoptotic cells, orchestrated through the interaction of numerous recognition or eat-me signals, bridging molecules, and engulfment receptors, is believed to prevent inadvertent immune responses to self-antigen present within or on the surface of dying cells. Indeed, the immune system is equipped with pattern recognition receptors to distinguish not only between foreign pathogens (non-self) and normal healthy tissues (self) but also to enable the discrimination between healthy viable cells (self) and dying cells (altered self) during the course of tissue remodeling or tissue injury.

The clearance of dead cell corpses by macrophages represents the final stage of apoptosis. Engulfment of apoptotic cells by phagocytes promotes the resolution of inflammation and prevents the autoimmune response associated with uncontrollable release of intracellular antigens. However, while an intact clearance system is critical to normal development and tissue homeostasis, it might present an obstacle to establishing immunity towards tumors, where cell loss by apoptosis is a common occurrence. For example, evidence suggests that uptake of apoptotic cells by macrophages promotes the release of immunosuppressive cytokines transforming growth factor-β1 (TGF-β) and IL-10.

A common feature of all eukaryotic membranes is the non-random (asymmetric) distribution of different lipid species in the lipid bilayer. One of the best known examples is the plasma membrane with its asymmetric distribution of aminophospholipids—phosphatidylserine (PS) and phosphatidylethanolamine (PE)—resulting in exclusive abundance or high prevalence of these phospholipids in the inner leaflet of the membrane in viable cells and their absence from the outer leaflet. The lack of these on the outer surface lipids, particularly PS, creates an opportunity for sensitive and specific PS signaling. PS and PS-OX, as well as other phospholipids such as oxidized phosphatidylcholine (PC-OX) are recognized by specific phagocyte receptors and contribute to the clearance of dying cells. Apoptotic cells that do not express PS fail to undergo efficient engulfment by macrophages, whereas the clearance defect can be restored by repleting the plasma membrane of target cells with exogenous PS.

Many potential receptors have been implicated in the recognition of dying cells, including the so-called PS receptor (PSR), various members of the integrin receptor and scavenger receptor families, as well as TIM-4 (T cell immunoglobulin- and mucin-domain-containing molecule-4) and the related protein, TIM-1, and several other molecules. PS-OX and, to a lesser extent, PC-OX may be specific signals for the scavenger receptor, CD36. The bridging molecule, MFG-E8 interacts preferentially with oxidized PS.

Recognition of exposed phosphatidylserine on apoptotic cellular membranes via homeostatic clearance receptors that transmit inhibitory signaling events provides a means for phagocytic cells to clear apoptotic corpses. This homeostatic clearance program, however, may limit the immunogenicity of apoptotic cells, and raises the possibility that altering clearance of dying cancer cells can potentiate immune responses against tumor cells. The present invention addresses this matter.

SUMMARY

Compositions and methods are provided for altering clearance mechanisms of cellular corpses to promote inflammatory turnover of apoptotic cells and enhance their immunogenicity. In the methods and compositions of the invention, engineered tether proteins link apoptotic cells to immunogenic receptors, thereby blocking homeostatic elimination of cells while simultaneously activating or disinhibiting immune pathways. This class of immune modulatory therapeutics are useful in promoting the elimination of cancer or pathogens and potentiate the therapeutic effect of cellular and molecular based therapies.

A tether protein of the invention comprises (a) a phosphatidylserine (PS) binding domain and (b) an immunostimulatory domain. The domains may be joined through a polypeptide linker, or may be chemically linked. The PS binding domain specifically binds to PS. Protein sequences of interest for this purpose include, without limitation, variable regions of antibodies that specifically bind PS, FA58C2 domain from the MFG-E8, PS binding domain of a TIM family protein, e.g. Tim-4, Tim-1, Tim-3; etc. Various protein sequences find use as an immunostimulatory domain, including without limitation an immunoglobulin Fc sequence that binds to and activates one or more FcγR, e.g. a human IgG1 Fc sequence. Other immunostimulatory sequences of interest include, for example, checkpoint inhibitors and immune agonists, e.g. anti-PD1, anti-PDL1, anti-CTLA4, CD40L, anti-CD47, anti-CD40, CD137 agonists; stimulatory interleukins, e.g. IL-2, IL-17; and ligands of immunomodulatory receptors on NK cells, cytotoxic T cells, γδ T cells, regulatory T cells, macrophages, monocytes, innate lymphocytes, dendritic cells, and the like. In some specific embodiments of the invention, a PS tether protein is provided, comprising a truncated MFG-E8 sequence that has deleted the native N terminal EGF domains containing RGD motifs; fused to the Fc region of human IgG1. In some embodiments a PS tether protein is provided, consisting of a PS binding domain from TIM1 or TIM4; fused to the Fc region of human IgG1.

In some embodiments, the PS tether polypeptide of the invention is provided in an engineered cell, where the cell has been genetically modified to secrete the PS tether polypeptide. In some such embodiments, the PS tether polypeptide is operably linked to an inducible promoter. The engineered cell may be an immune cell, e.g. B cell, T cell, macrophage, etc. In some embodiments the engineered cell is a T cell comprising an engineered T cell receptor, e.g. a TCR specific for a tumor antigen, a pathogen antigen, etc.

An individuals that can be treated with a PS tether polypeptide include individuals that have cancer, individuals that harbor an infection, e.g., a chronic infection, a viral infection, etc.; and the like. A dose of the PS tether polypeptide, or an engineered cell expressing a PS tether polypeptide, is administered, which dose enhance immune responsiveness against a targeted cell population. The targeted cell population may be a cancer cell population, a virus infected population, etc., where the targeted cells have increased levels of apoptosis relative non-targeted cells. In some embodiments, the PS tether polypeptide is combined with a therapy that increases apoptosis of the targeted cell population, e.g. radiation therapy, alkylating chemotherapy, antibody therapy, and the like. In some embodiments, the PS tether polypeptide is combined with a therapy that enhances activation of an immune response against the targeted cell population, e.g. checkpoint inhibitor therapy, administration of an engineered T cell population, administration of an agent that agonizes an immune costimulatory molecule, e.g. CD137; and the like. In some embodiments a PS tether protein is administered in combination with an effective dose of an immunogen, e.g. an immunogenic dose of cancer cells; an immunogenic dose of virus or other pathogen, and the like.

The disclosure also includes pharmaceutical formulations having a PS tether polypeptide in combination with a pharmaceutically acceptable excipient (a pharmaceutical excipient). Such formulations may be provided as a unit dose (a unit dose formulation), e.g. a dose effective to stimulate antigen presenting cell (APC) activity. Pharmaceutical formulations also include lyophilized or other preparations of the PS tether polypeptides, which may be reconstituted for use.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A, Schematic depicting generation of an anti-phosphatidylserine fusion protein. The PS binding domain (FA58C2) from the secreted PS binding bridge protein, MFG-E8, was fused to the Fc fragment of human IgG1. FIG. 1B, Anti-PS bridge proteins alter immune homeostasis in the tumor microenvironment by promoting inflammatory turnover of apoptotic cells. FIG. 1C, Murine lymphocytes preincubated with dexamethasone to induce apoptosis were labeled with C2-hIgG1 and analyzed with the Amnis ImageStream cytometer. Fusion protein was detected using flourophore labeled goat anti-human antibody. FIG. 1D, OT-I T cells were CFSE labeled and adoptively transferred into congenic strains and challenged via subcutaneous injection by Ova-expressing EG7 cells. Prior to injection, cells were randomized to undergo apoptosis and surface bound with anti-phosphatidylserine fusion protein. Three days later draining lymph nodes (dLNs) were harvested and analyzed by FACs. FIG. 1E, Proliferation of OT-I T cells in dLNs was measured by FACS and displayed as histogram plots. Blockade of homeostatic removal programs with an anti-phosphatidylserine fusion protein promotes crosspresentation of apoptotic tumor cells.

FIG. 2A-2B, Groups of C3H/HeN mice were injected with 38c13 lymphoma cells and treated with anti-phosphatidylserine fusion protein or isotype control. Intratumoral therapy was initiated five days following tumor challenge. Treated groups were injected with α-CTLA-4 alone or in combination with anti-phosphatidylserine fusion protein. Complete Responses (CRs) occurred in 50% of mice receiving combination therapy, whereas animals that received α-CTLA-4 alone were unresponsive to therapy. FIG. 2B, Corresponding Kaplan-Meier survival curves among treatment groups. A Log-rank test was used for survival analysis. FIG. 2C-2D, Tumor sizes of Balb/c mice injected with A20 lymphoma cells and treated with anti-phosphatidylserine fusion protein or isotype control. FIG. 2D, Corresponding Kaplan-Meier survival curves among treatment groups.

FIG. 3A-3G. Treatment with an anti-phosphatidylserine fusion protein expands infiltrating T cells and reduces regulatory T and myeloid cells within 38c13 lymphoma tumors. FIG. 3A, Heat map showing relative abundance of immune cells from tumors under treatment with an anti-phosphatidylserine fusion protein or isotype control. FIG. 3B, Change in T cell subsets or their ratio after initiation of therapy. Red line is mean. FIG. 3C, Representative contour plots of Ki67 and Gzm B staining (top) or PD1 (bottom) among $CD8^+$ TILs after treatment with α-CTLA-4, C2-hIgG1, or the combination of α-CTLA-4+C2-hIgG1. FIG. 3D, Proportion of $CD8^+$ TILs that are either $Ki67^+$ and Gzm $B^+$ or $Ki67^-$ and Gzm $B^-$, $PD1^+$, or Interferon $\gamma^+$. FIG. 3E, Change in $CD3^-$ $NkP46^+$ NK cells and $CD11c^+$ $CD11b^+$ Dendritic Cell frequency. Values are relative to untreated controls. FIG. 3F, Representative Interferon γ contour plots after treatment with α-CTLA-4, C2-hIgG1, or the combination of α-CTLA-4+C2-hIgG1. FIG. 3G, Immunofluorescent staining from corresponding tumor biopsies.

FIG. 4A-4G. In vitro characterization of cellular-based CTL delivery of a cross priming reagent FIG. 4A, An anti-phosphatidylserine fusion protein was combined with an IL-2 leader peptide sequence and inserted into a retroviral cassette. Anti-CD3/CD28 activated OT-I T cells were transduced with retrovirus and cocultured with Ova-expressing EG7 target cells. FIG. 4B, ELISA for total hIgG secretion of 24 h-collection supernatents of OT-$I^{WT}$ and OT-$I^{C2-hIgG1}$ transduced T cells. FIG. 4C, In vitro cytotoxicity assay against the EG7 target cell line shows target cells but not effector cells coated with secreted protein (top). Cells stained with anti-human IgG. The assay was performed 7 days after initial T cell activation. FIG. 4D, Specific lysis activity among OT-$I^{WT}$ and OT-$I^{C2-hIgG1}$ transduced T cells. The cytolytic activity of the OT-$I^{C2-hIgG1}$ was comparable to that of OT-$I^{WT}$ cells. FIG. 4E, Amnis ImageStream microscopy of an immune synapse showing target cell death induced by OT-$I^{C2-hIgG1}$ transduced T cells. The image shows a target cell covered with engineered secreted protein. FIG. 4F, EG7 target cells display both diffuse and FIG. 4G clustered membrane staining of secreted protein.

FIG. 5B, Tumor sizes in mice adoptively transferred with 4×10$^6$ OT-I$^{WT}$ or OT-I$^{C2-hIgG1}$ transduced T cells. 63.6% of mice treated with OT-I$^{C2-hIgG1}$ achieved durable, complete responses (CRs) compared to 40.9% in OT-I$^{WT}$ animals (p<0.001). Error bars represent standard error of the mean. FIG. 5C, Kaplan Meier survival analysis among treatment groups. FIG. 5D, Mice were rechallenged with EG7 cells 90 days after initial tumor inoculation. Survivors were then challenged with 1×10$^6$ parental, non-ova expression EL4 tumor cells. FIG. 5E, Results of EL4 challenge experiments FIG. 5F, Results of EG7 re-challenge experiments FIG. 5G, Transfer of OT-I$^{C2-hIgG1}$ T cells was associated with increased protection to EL4 tumor challenge [OR=0.185, p=0.04].

FIG. 6A, a bi-cistronic retroviral vector encoding both a CD19-specific CAR (1928z) and C2-hIgG preceded by an IL-2 signal peptide sequence (1928z/C2-hIgG T cells) was introduced into activated C3H/HeN splenocytes. FIG. 6B, In vitro cytotoxicity assay of 1928z/C2-hIgG CAR T cells against 38c13 murine B cell lymphoma cells. FIG. 6C, Seven days after initial activation 6×10$^6$ CAR T cells were adoptively transferred into C3H/HeN mice bearing established 38c13 lymphomas. Growth curves in syngeneic mice show no significant difference in treatment outcomes between the groups.

FIG. 7A-7B. Treatment with C2-hIgG1 reduces the growth of murine 38c13 lymphoma cells. FIG. 7A, Groups of mice were injected subcutaneously with 0.5×10$^6$ 38c13 lymphoma cells. Treated groups were injected intraperitonally with 200 μg of C2-hIgG1 or irrelevant hIgG1 control antibody q.o.d for days 1-14. Anti-CTLA-4 antibody (200 μg each) was administered by i.p injection on days two, four, and seven after tumor inoculation. FIG. 7B, Anti-CD8, anti-CD4 depleting mAbs, and asialo GM1 were used to deplete CD4, CD8, and NK cells. Depleting antibodies were injected i.p. on day −1 and day 0 of tumor inoculation, and every 5 days thereafter at dose of 250 μg per injection while under treatment with C2-hIgG1.

DETAILED DESCRIPTION OF THE EMBODIMENTS

Figure 1A:
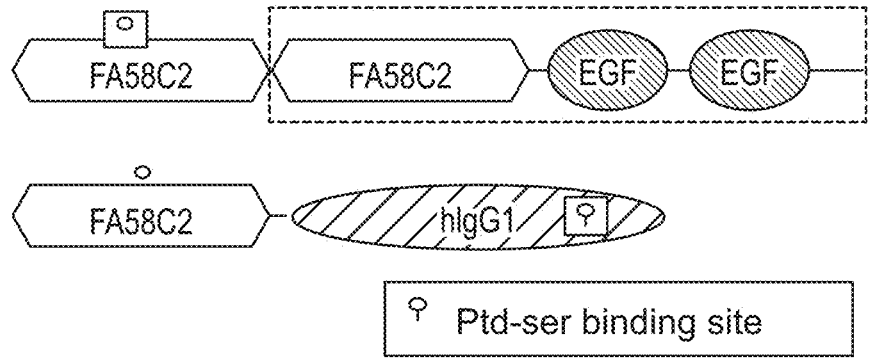
FIG. 1A-1E. Characterization of cross-presentation of tumor antigens with an anti-phosphatidylserine fusion protein.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias.

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer is a suitable cancer to be treated by the subject methods and compositions.

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratoma is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of disease progression (e.g., cancer-attributable death or progression), including recurrence, metastatic spread of cancer, and drug resistance. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_d$ (dissociation constant) of $10^{-6}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_d$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the disclosure.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use in addition to those for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this disclosure can be present in unsalified or unesterified form, or in salified and/or esterified form, and the naming of such compounds is intended to include both the original (unsalified and unesterified) compound and its pharmaceutically acceptable salts and esters. Also, certain compounds named in this disclosure may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The term "target cell" as used herein refers to a cell targeted for destruction by the immune system after administration of a subject PS tether polypeptide. Administration of a subject PS tether polypeptide leads to stimulation of the immune system (via stimulation of APC activity), thereby leading to the destruction of the target cell. In some cases, a target cell expresses a receptor (or counter receptor) for BTN3A. In some cases, the target cell is determined by the interactions of the APC and the naive T-cell (e.g., determined by the antigen(s) that are presented by the APC(s)).

In some cases, a target cell is an "inflicted" cell (e.g., a cell from an "inflicted" individual), where the term "inflicted" is used herein to refer to a subject with symptoms, an illness, or a disease that can be treated with a PS tether polypeptide. An "inflicted" individual can have cancer, can harbor an infection (e.g., a chronic infection), etc. "Inflicted cells" can be those cells that cause the symptoms, illness, or disease. As non-limiting examples, the inflicted cells of an inflicted patient can be cancer cells, infected cells, inflammatory cells, and the like.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, etc.) A therapeutic treatment is one in which the subject is inflicted prior to administration and a prophylactic treatment is one in which the subject is not inflicted prior to administration.

The word "label" when used herein refers to a detectable compound or composition which is conjugated directly or indirectly to a subject PS tether polypeptide. The label may itself be directly detectable (detectable by itself, e.g., radioisotope labels, fluorescent labels, etc.) or can be detected indirectly (e.g., an enzymatic label, which may catalyze chemical alteration of a substrate compound or composition which is detectable).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, $IgA_2$. The heavy-chain constant domains (Fc) that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

Fc Receptors.

The human IgG receptor family consists of a number of high affinity Fcγ receptors, including hFcγRI, hFcγRIIA, hFcγRIIC, hFcγRIIIA, hFcγRIIB, hFcγRIIIB; and a low affinity receptor, hFcRn, involved in recycling and transport of IgG. Expression of the Fc receptors varies among immune effector cells. hFcγRI (CD64) is restricted to monocytes/macrophages and dendritic cells (DCs) and, inducibly, expressed on neutrophils and mast cells; hFcγRIIA (CD32A) is expressed on all myeloid cells but not on lymphocytes; hFcγRIIB (CD32B) is highly expressed only on circulating B cells and basophils and expressed on tissue macrophages and DCs, but not on mast cells; hFcγRIIC (CD32C) is expressed on NK cells, monocytes, and neutrophils; hFcγRIIIA (CD16A) is expressed on NK cells and monocytes/macrophages; hFcγRIIIB (CD16B) is expressed on neutrophils and subsets of basophils.

Fc Domain or Region.

The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Engineering the Fc region of a therapeutic monoclonal antibody or Fc fusion protein allows the generation of molecules that are better suited to the pharmacology activity required of them.

A "wild-type Fc region" possesses the effector functions of a native-sequence Fc region, in particular for the purposes of the present invention interacting with one or more of the high affinity receptors e.g. the FcγRI; FcγRIIA; FcγRIIB1; FcγRIIB2; FcγRIIIA; FcγRIIIB receptors; and can be assessed using various assays as disclosed, for example, in definitions herein. The amino acid sequence may be identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" or "engineered Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Proteins of the invention may have an Fc sequence with enhanced effector functions, e.g. by increasing their binding capacities to FcγRIIIA and increasing ADCC activity. For example, fucose attached to the N-linked glycan at Asn-297 of Fc sterically hinders the interaction of Fc with FcγRIIIA, and removal of fucose by glyco-engineering can increase the binding to FcγRIIIA, which translates into >50-fold higher ADCC activity compared with wild type IgG1 controls. Protein engineering, through amino acid mutations in the Fc portion of IgG1, has generated multiple variants that increase the affinity of Fc binding to FcγRIIIA. Notably, the triple alanine mutant S298A/E333A/K334A displays 2-fold increase binding to FcγRIIIA and ADCC function. S239D/I332E (2X) and S239D/I332E/A330L (3X) variants have a significant increase in binding affinity to FcγRIIIA and augmentation of ADCC capacity in vitro and in vivo. Other Fc variants identified by yeast display also showed the improved binding to FcγRIIIA and enhanced tumor cell killing in mouse xenograft models. See, for example Liu et al. (2014) JBC 289(6):3571-90, herein specifically incorporated by reference.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Polypeptides

A tether protein of the invention comprises (a) a phosphatidylserine (PS) binding domain and (b) an immunostimulatory domain. The PS binding domain specifically binds to PS. Protein sequences of interest for this purpose include, without limitation, variable regions of antibodies that specifically bind PS, FA58C2 domain from the MFG-E8, PS binding domain of a TIM family protein, e.g. Tim-4, Tim-1, Tim-3; etc. Various protein sequences find use as an immunostimulatory domain, including without limitation an immunoglobulin Fc sequence that binds to and activates one or more FcγR, e.g. a human IgG1 Fc sequence. Other immunostimulatory sequences of interest include, for example, checkpoint inhibitors and immune agonists, e.g. anti-PD1, anti-PDL1, anti-CTLA4, CD40L, anti-CD47, anti-CD40, CD137 agonists; stimulatory interleukins, e.g. IL-2, IL-17; and ligands of immunomodulatory receptors on NK cells, cytotoxic T cells, γδ T cells, regulatory T cells, macrophages, monocytes, innate lymphocytes, dendritic cells, and the like. In some specific embodiments of the invention, a PS tether protein is provided, comprising a truncated MFG-E8 sequence that has deleted the native N terminal EGF domains containing RGD motifs; fused to the Fc region of human IgG1. In some embodiments a PS tether protein is provided, consisting of a PS binding domain from TIM1 or TIM4; fused to the Fc region of human IgG1.

In some embodiments, a subject PS tether polypeptide includes a linker (e.g., a linker polypeptide), e.g. between the PS binding domain and the immunostimulatory domain. A linker polypeptide may have any of a variety of amino acid sequences. Proteins can be joined by a linker polypeptide can be of a flexible nature (e.g., a flexible linker polypeptide), although other chemical linkages are not excluded. Suitable linkers include polypeptides of between about 6 amino acids and about 40 amino acids in length, or between about 6 amino acids and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that the in some case, linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

In some embodiments a tether polypeptide comprises a sequence set forth in SEQ ID NO:1, 2 or 3, or a polynucleotide encoding the same. In some embodiments a PS tether polypeptide has at least about 80% sequence identity to SEQ ID NO: 1, 2 or 3, at least about 85% sequence identity, at least about 90% sequence identity, at least about 95% sequence identity, at least about 99% sequence identity.

Examples of linker polypeptides include glycine polymers $(G)_n$, glycine-serine polymers (including, for example, $(GS)_n$, GSGGSn (SEQ ID NO: 4), GGSGGSn (SEQ ID NO: 5), and GGGSn (SEQ ID NO: 6), where n is an integer of at least one (e.g., where n is an integer of one, two, three, four, five, six, seven, eight, nine, ten, or greater than ten), glycine-alanine polymers, alanine-serine polymers. Exemplary linkers can comprise amino acid sequences including, but not limited to, GGSG (SEQ ID NO: 7), GGSGG (SEQ ID NO: 8), GSGSG (SEQ ID NO: 9), GSGGG (SEQ ID NO: 10), GGGSG (SEQ ID NO:11), GSSSG (SEQ ID NO: 12), and the like. The ordinarily skilled artisan will recognize that design of a peptide conjugated to any elements described above can include linkers that are all or partially flexible, such that the linker can include a flexible linker as well as one or more portions that confer less flexible structure.

In some other embodiments, PS tether polypeptides of the disclosure include reagents further modified to improve their resistance to proteolytic degradation or to optimize solubility properties or to render them more suitable as a therapeutic agent. For example, variants of the present disclosure further include analogs containing residues other than naturally occurring L-amino acids, e.g. D-amino acids or non-naturally occurring synthetic amino acids. D-amino acids may be substituted for some or all of the amino acid residues.

Producing a PS Tether Polypeptide

PS tether polypeptides of the present disclosure can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA encoding the polypeptides of interest may be chemically synthesized or transcribed in vitro. One of skill in the art can readily utilize well-known codon usage tables and synthetic methods to provide a suitable coding sequence for any of the polypeptides of the disclosure. The nucleic acids may be isolated and obtained in substantial purity. The nucleic acids, either as DNA or RNA, can be obtained substantially free of other nucleic acid sequences, generally being at least about 50%, usually at least about 90% pure. Subject nucleic acids can be "recombinant," e.g., flanked by one or more nucleotides with which it is not normally associated on a naturally occurring chromosome. The nucleic acids of the disclosure can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the disclosure can be introduced into suitable host cells using a variety of techniques available in the art.

Nucleic Acids and Production of a PS Tether Polypeptide

Compositions are provided that include a nucleic acid (e.g., RNA or DNA) encoding a subject PS tether polypeptide (i.e., a nucleic acid that includes a nucleotide sequence that encodes a subject PS tether polypeptide). The sequence encoding a subject PS tether polypeptide can be operably linked to a promoter operable in a desired cell type (e.g., a prokaryotic cell, a eukaryotic cell, a eukaryotic cell of a particular tissue type, a mammalian cell, a human cell, etc.).

The disclosure also provides isolated nucleic acids encoding a subject PS tether polypeptide, vectors and host cells comprising the nucleic acid, and recombinant techniques for the production of PS tether polypeptides.

For recombinant production of a subject PS tether polypeptide, a nucleic acid encoding the PS tether polypeptide can be inserted into a replicable vector for further cloning (amplification of the DNA) or for expression. DNA encoding a subject PS tether polypeptide can be readily isolated and sequenced using conventional procedures. Many vectors are available. The vector components can include, but are not limited to, one or more of the following: a signal sequence (i.e., a nucleotide sequence encoding a signal sequence that will be fused in frame with the PS tether polypeptide, which provides for secretion of the PS tether polypeptide), an origin of replication, one or more marker genes, an enhancer element, a promoter, and a transcription termination sequence.

A PS tether polypeptide of this disclosure may be produced recombinantly not only directly, but also as a fusion polypeptide with a heterologous polypeptide, which can include a signal sequence or other polypeptide having a specific cleavage site at the N-terminus of the mature protein or polypeptide. Thus, a PS tether polypeptide can include a signal sequence, which is generally cleaved away from the protein during secretion from a cell. A signal sequence can be any polypeptide (amino acid sequence) that is recognized and processed (i.e., cleaved by a signal peptidase) by the host cell. For prokaryotic host cells that do not recognize and process a native eukaryotic signal sequence, the signal sequence can be substituted by a prokaryotic signal sequence.

An "isolated" nucleic acid molecule is a nucleic acid molecule that is identified and separated from at least one contaminant nucleic acid molecule with which it is ordinarily associated prior to isolation. An isolated nucleic acid molecule is other than in the form or setting in which it can be found in nature. Isolated nucleic acid molecules therefore are distinguished from the nucleic acid molecule as it exists in natural cells. In the present disclosure, a PS tether polypeptide by definition is not naturally occurring.

Examples of suitable host cells for cloning or expressing subject nucleic acids include, but are not limited to prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells can be transformed with the above-described expression or cloning vectors for PS tether polypeptide production and cultured in conventional nutrient media modified as appropriate for inducing promoters, selecting transformants, or amplifying the genes encoding the desired sequences.

Introduction of Nucleic Acids

In some cases, a subject PS tether polypeptide is administered to an individual (and/or introduced into a cell) by providing the PS tether polypeptide as a nucleic acid (e.g., an RNA, e.g., an mRNA; or a DNA, e.g., a recombinant expression vector, a linear DNA, a circular DNA, a plasmid, a viral vector, etc.) encoding the PS tether polypeptide. This disclosure provides such methods and also the nucleic acids for such methods.

For example, an mRNA encoding a subject PS tether polypeptide can be introduced into a cell, and the cell can then secret the translated protein. As another example, a DNA (e.g., a recombinant expression vector, a linear DNA, a circular DNA, a plasmid, a viral vector, etc.) encoding a subject PS tether polypeptide can be introduced into a cell and the cell can then produce and secret the encoded protein. Therefore, in some cases, a nucleic acid encoding a subject PS tether polypeptide includes a nucleotide sequence encoding a signal sequence (e.g., upstream of and in frame with the nucleotide sequence that encodes the PS tether polypeptide). As would be readily recognized by one of ordinary skill in the art, a signal sequence as referred to here is an amino acid sequence at or near the amino terminus of a nascent protein that can be recognized by the signal recognition particle of a eukaryotic cell, resulting in transport of the protein into the secretory pathway of the cell, thus facilitating secretion of a protein from the cell (e.g., the signal sequence can be cleaved from the protein). Any convenient signal sequence can be used.

In some cases, a nucleic acid encoding a subject PS tether polypeptide is introduced into a cell (e.g., in vivo, ex vivo, in vitro) and the cell can then produce and secret the encoded protein. In some cases, the cell is in vitro. In some cases, the cell is ex vivo. In some cases, the cell is in vivo (e.g., in some cases, a nucleic acid encoding a subject PS tether polypeptide is administered to an individual, e.g., systemically, locally, injected, injected intratumorally, injected locally, etc.). For example, in some cases, a nucleic acid encoding a PS tether polypeptide is introduced into a cell that is in vivo (e.g., in some cases, a nucleic acid encoding a PS tether polypeptide is introduced into a cell in vivo by administering the nucleic acid to an individual). In some cases, a nucleic acid encoding a subject PS tether polypeptide is introduced into a cell (e.g., ex vivo, in vitro) and the cell is then introduced into an individual. In some cases, the cell is autologous to the individual (e.g., the cell was isolated from the individual or is the progeny of a cell that was isolated from the individual).

In some cases (e.g., in any of the above scenarios, e.g., in vitro, ex vivo, in vivo), the cell into which a nucleic acid encoding a subject PS tether polypeptide is introduced is an immune cell (e.g., a leukocyte, a T cell, a CD8 T cell, a CD4 T cell, a memory/effector T cell, a B cell, a myeloid cell, an antigen presenting cell (APC), a dendritic cell, a macrophage, a monocyte, an NK cell, and the like). In some cases (e.g., in any of the above scenarios, e.g., in vitro, ex vivo, in vivo), the cell into which a nucleic acid encoding a subject PS tether polypeptide is introduced is a stem cell (e.g., a hematopoietic stem cell, a pluripotent stem cell, a multipotent stem cell, a tissue restricted stem cell, a self-renewing T cell, a long term memory T cell, etc.). In some cases (e.g., in any of the above scenarios, e.g., in vitro, ex vivo, in vivo), the cell into which a nucleic acid encoding a subject PS tether polypeptide is introduced is an immune cell (e.g., a lymphocyte, a leukocyte, a T cell, a CD8 T cell, a CD4 T cell, a regulatory T cell, a memory T cell, an effector T cell, a memory/effector T cell, a B cell, an antigen presenting cell (APC), a dendritic cell, a macrophage, a monocyte, an NK cell, and the like) or a stem cell (e.g., a hematopoietic stem cell, a pluripotent stem cell, a multipotent stem cell, a tissue restricted stem cell, a self-renewing T cell, a long term memory T cell, etc.). In some cases (e.g., in any of the above scenarios, e.g., in vitro, ex vivo, in vivo), the cell into which a nucleic acid encoding a subject PS tether polypeptide is introduced is a cancer cell (e.g., a subject nucleic acid can be introduced into a tumor, i.e., into a cell of a tumor).

In some cases (e.g., in any of the above scenarios, e.g., in vitro, ex vivo, in vivo), the cell into which a nucleic acid encoding a subject PS tether polypeptide is introduced is a T cell with an engineered T cell receptor (TCR) (such a cell is also referred to herein as a "TCR-engineered T cell"). As used herein the term "TCR-engineered T cell" refers to any T-cell having a T cell receptor that is heterologous to the T cell. Suitable examples include, but are not limited to (i) a T cell that includes a chimeric antigen receptor (CAR) (such a cell is also referred to herein as a "CAR-T cell" or an "engineered CAR-T cell"); and (ii) a T cell that includes a heterologous TCR that binds to an antigen such as a cancer antigen, e.g., MART1, NY-ESO-1, p53, and the like (e.g., such a cell can include a nucleic acid encoding the TcR-alpha and TcR-beta polypeptides of a heterologous TCR, such as a TCR that binds to an antigen such as a cancer antigen, e.g., MART1, NY-ESO-1, p53, and the like). In some cases, a T cell that includes a chimeric antigen receptor (CAR) is an 'armored CAR T cell (e.g., a CAR-containing T cell that secretes one or more cytokines).

In some cases, a suitable TCR-engineered T cell can have an engineered TCR (e.g., a CAR, a heterologous TCR that binds to an antigen, etc.) that binds to a cancer marker (e.g., CD19, CD20, CD22, CD24, CD25, CD30, CD33, CD38, CD44, CD52, CD56, CD70, CD96, CD97, CD99, CD123, CD279 (PD-1), PDL1, ROR1, EGFR, HER2, CD117, C-Met, PTHR2, and/or HAVCR2 (TIM3)). In some cases, a suitable TCR-engineered T cell can have an engineered TCR (e.g., a CAR, a heterologous TCR that binds to an antigen, etc.) that binds to a target antigen (e.g., any desired target antigen).

A "vector" or "expression vector" is a replicon, such as plasmid, phage, virus, or cosmid, to which another DNA segment, i.e. an "insert", may be attached so as to bring about the replication of the attached segment in a cell. An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" or "expression vector" and similar terms of the art are used interchangeably herein to refer to a DNA molecule comprising a vector and at least one insert. Recombinant expression vectors can be generated for the purpose of expressing and/or propagating the insert(s), or for the construction of other recombinant nucleotide sequences. The insert(s) (e.g., a nucleotide sequence encoding a subject PS tether polypeptide) may or may not be operably linked to a promoter sequence and may or may not be operably linked to DNA regulatory sequences. Thus in some cases, a nucleotide sequence encoding a subject PS tether polypeptide is operably linked to a promoter (e.g., one that is operable in a desired cell type, e.g., a eukaryotic cell, a mammalian cell, a primate cell, a human cell, an immune cell, a leukocyte, a T cell, a CD8 T cell, a CD4 T cell, a memory/effector T cell, a B cell, an antigen presenting cell (APC), a dendritic cell, a macrophage, a monocyte, an NK cell, a stem cell, a hematopoietic stem cell, a pluripotent stem cell, a multipotent stem cell, a tissue restricted stem cell, etc.).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject site-directed modifying polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

Also provided in this disclosure are cells that include a nucleic acid (e.g., as described above) that includes a nucleotide sequence encoding a subject PS tether polypeptide. Such a cell can be a cell from any organism (e.g., a bacterial cell, an archaeal cell, a cell of a single-cell eukaryotic organism, a plant cell, an algal cell, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Pharmaceutical Compositions

According to the present disclosure, PS tether polypeptides (and/or a nucleic acid encoding the same) can be provided in pharmaceutical compositions (pharmaceutical formulations) suitable for therapeutic use, e.g. for human treatment. In some embodiments, pharmaceutical compositions of the present disclosure include one or more therapeutic entities of the present disclosure or pharmaceutically acceptable salts, esters or solvates thereof. In some other embodiments, pharmaceutical compositions of the present disclosure include one or more therapeutic entities of the present disclosure in combination with another therapeutic agent, e.g., an anti-tumor agent.

Therapeutic entities of the present disclosure (e.g., a PS tether polypeptide) may be administered as pharmaceutical compositions (pharmaceutical formulations) comprising an active therapeutic agent (e.g., a subject PS tether polypeptide) and a pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some cases, a subject composition (e.g., a therapeutic composition) consists of a PS tether polypeptide. In some cases, a subject composition (e.g., a therapeutic composition) consists essentially of a PS tether polypeptide. In some cases, a subject composition (e.g., a therapeutic composition) consists of a PS tether polypeptide and a pharmaceutically acceptable excipient. In some cases, a subject composition (e.g., a therapeutic composition) consists essentially of a PS tether polypeptide and a pharmaceutically acceptable excipient.

In still some other embodiments, pharmaceutical compositions of the present disclosure can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Methods of Use

Aspects of the disclosure include methods and compositions for inducing an immune response in an individual. For example, aspects of the disclosure include methods and compositions for activating an immune response against apoptotic cells, including without limitation tumor cells. Methods are provided for treating, reducing and/or or preventing cancer; treating, reducing and/or or preventing infection (e.g., chronic infection), etc. For example, in some cases, a subject PS tether polypeptide can be used as an immune stimulant (e.g., used for immunopotentiation) in combination with a second agent, e.g. an antibody specific for a tumor cell antigen, an immune checkpoint inhibitor, an immune agonist, e.g. anti-CD137 agonist, etc. In some cases, a subject method is a method of treating an individual having cancer and/or having a chronic infection.

For example, a subject composition can be administered to an individual (e.g., systemically or locally, e.g., injected into or near a tumor, into or near a site of tumor resection, and the like) and endogenous immune cells, including phagocytic cells, are thereby contacted with the PS tether polypeptide. The activated immune cells can then contact endogenous immune effector cells in vivo. As noted above, methods of treating, contacting, etc. can be performed by introducing a nucleic acid encoding a subject PS tether polypeptide into a cell (e.g., administering such a nucleic acid to an individual, introducing such a nucleic into a cell and then introducing/administering the cell into an individual, etc.)

In some cases, methods of treating can include a step of administering to the individual a PS tether polypeptide (e.g., in an amount (e.g., in a unit dose formulation) that is effective to treat the individual, e.g., reduce the number of cancer cells, reduce the number of infected cells, increase the number of activated APCs, increase the number of activated T cells, increase activity level of the immune system, and the like).

The number of administrations of treatment to a subject may vary. Introducing cells and/or compositions into an individual may be a one-time event; but in certain situations, such treatment may elicit improvement for a limited period of time and require an on-going series of repeated treatments. In other situations, multiple administrations of cells and/or compositions may be required before an effect is observed. As will be readily understood by one of ordinary skill in the art, the exact protocols depend upon the disease or condition, the stage of the disease and parameters of the individual being treated.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of cells and/or compositions is an amount that is sufficient, when administered to (e.g., transplanted into) the individual, to palliate, ameliorate, stabilize, reverse, prevent, slow or delay the progression of the disease state (e.g., tumor size, tumor growth, tumor presence, cancer presence, etc.) by, for example, inducing an immune response against antigenic cells (e.g., cancer cells).

The compositions of this disclosure can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

The subject therapeutic agents (e.g., a subject PS tether polypeptide) can activate immune cells (e.g., monocytes and APCs such as dendritic cells, macrophages, and B cells; and therefore T cells), and therefore enhance immune cell functions such as inhibiting cancer cell growth and/or viral infection, and restore immune surveillance and immune memory function to treat human disease. Examples of symptoms, illnesses, and/or diseases that can be treated with a subject PS tethe rpolypeptide include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); etc. For example, in some cases, a PS tether polypeptide can be used as an immune stimulant (e.g., used for immunopotentiation).

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

For example, "concomitant administration" of a therapeutic agent, e.g., cancer therapeutic drug, e.g., a tumor-directed antibody; an immune-oncology antibody such as a checkpoint inhibitor, an immune agonist, a therapeutic drug to treat an infection; etc. with a subject polypeptide (e.g., as a pharmaceutical composition) of the present disclosure means administration with a subject polypeptide at such time that both the therapeutic agent and the subject polypeptide will have a therapeutic effect. Such concomitant administration may involve concurrent (i.e. at the same time), prior, or subsequent administration of the therapeutic agent with respect to the administration of the PS tether polypeptide. A person of ordinary skill in the art would have no difficulty determining the appropriate timing, sequence and dosages of administration for particular drugs and compositions of the present disclosure.

Because a subject PS tether polypeptide activates APCs and stimulates the immune system, in some cases, the agent which is co-administered with the PS tether polypeptide can be administered at a dose that is lower when the agent is administered in the absence of the PS tether polypeptide. In some cases, the agent which is co-administered with the PS tether polypeptide is administered at a dose that is considered sub-therapeutic when the agent is administered in the absence of the PS tether polypeptide. In some cases, the agent which is co-administered with the PS tether polypeptide is an agent that is not effective when administered without the PS tether polypeptide. Thus, co-administration with a PS tether polypeptide can render agents effective that in the past have been considered to be ineffective.

In some embodiments, a subject PS tether polypeptide is administered in combination (co-administration) with another agent, e.g., an immune stimulant, an APC stimulatory agent, an agent to treat chronic infection, a cytotoxic agent, a vaccine, a BiTE (bispecific T cell engaging) antibody, a chimeric antigen receptor (CAR)/TCR-engineered T cell, and the like, e.g.a gents that block the binding of CD47 on a first cell to SIRPa on a second cell (e.g., a binding protein (or fragment thereof) that binds to CD47, e.g., an anti-CD47 antibody, a SIRPa polypeptide derived from the ectodomain of SIRPa, etc.; a binding protein (or fragment thereof) that binds to SIRPa, e.g., an anti-SIRPa antibody, a CD47 polypeptide derived from the ectodomain of CD47, etc.); or alternatively or in combination with a Toll-like receptor (TLR) agonist; (ii) a CD40 agonist and a proinflammatory cytokine; (iii) a checkpoint molecule neutralizing compound; (iv) an indoleamine 2,3-dioxygenase (IDO) inhibitor; (v) an NFkB activator; (vi) a compound that opens calcium channels; (vii) a T cell-related co-stimulatory molecule; or (viii) a combination thereof. In some cases, the TLR agonist is CpG ODN, immunostimulatory DNA, immunostimulatory RNA, immunostimulatory oligonucleotides, Imiquimod, Resiquimod, Loxribine, Flagellin, FSL-I or LPS.

One example class of cytotoxic agents are chemotherapeutic agents. Exemplary chemotherapeutic agents include, but are not limited to, an anti-CD47 antibody, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

A subject PS tether polypeptide can be co-administered with an agent (e.g., an antibody) that specifically binds to a target molecule including, without limitation, CD19, CD20, CD22, CD24, CD25, CD30, CD33, CD38, CD44, CD52, CD56, CD70, CD96, CD97, CD99, CD123, CD279 (PD-1), PD-L1, EGFR, HER2, CD117, C-Met, PTHR2, HAVCR2 (TIM3), etc. Examples of antibodies with CDRs that provide specific binding to a cancer cell marker (and therefore can be used in a combination therapy (co-administered with a subject PS tether polypeptide) include, but are not limited to: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30).

In some cases, a subject PS tether polypeptide is co-administered with a T cell with an engineered T cell receptor (TCR) (such a cell is also referred to herein as a "TCR-engineered T cell"). Non-limiting suitable examples of a TCR-engineered T cell are: (i) a T cell that includes a chimeric antigen receptor (CAR); and (ii) a T cell that includes a heterologous TCR that binds to an antigen such as a cancer antigen.

A subject PS tether polypeptide can be co-administered with any convenient immunomodulatory agent (e.g., an anti-CTLA4 antibody, an anti-PD-1 antibody, a CD40 agonist, a 4-1BB modulator (e.g., a 41BB-agonist), and the like).

Effective doses of the therapeutic entity of the present disclosure (e.g., PS tether polypeptide), e.g. for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every day, or once every two days, or once every week, or once every two weeks, or once a month, or once every two months, or once every 3 to 6 months. Therapeutic entities of the present disclosure are usually administered on multiple occasions. Intervals between single dosages can be weekly, monthly or yearly. Intervals can also be irregular as indicated by measuring blood levels of the therapeutic entity in the patient. Alternatively, therapeutic entities of the present disclosure can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present disclosure include treating, reducing or preventing any of the above discussed conditions, ailments, and/or diseases (e.g., tumor growth, tumor metastasis or tumor invasion of cancers including lymphomas, leukemias, carcinomas, melanomas, glioblastomas, sarcomas, myelomas, etc.). For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the PS tether polypeptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Super Cross-Presentation of Tumor Antigens by Synthetic Design of an Anti-Phosphatidylserine Bridge Protein Phosphatidylserine (PS) is a crucial regulatory factor within the tumor microenvironment. Translocation of PS to the outer leaflet of the plasma membrane can rapidly increase under pathophysiological conditions, triggering engulfment and preventing secondary necrosis and inflammation in the surrounding tissue. These protective effects have been shown to shield bystander cells and tissues from excessive immune-mediated damage—a process that that has been associated with the generation of an immunosuppressed tumor niche.

Figure 1B:
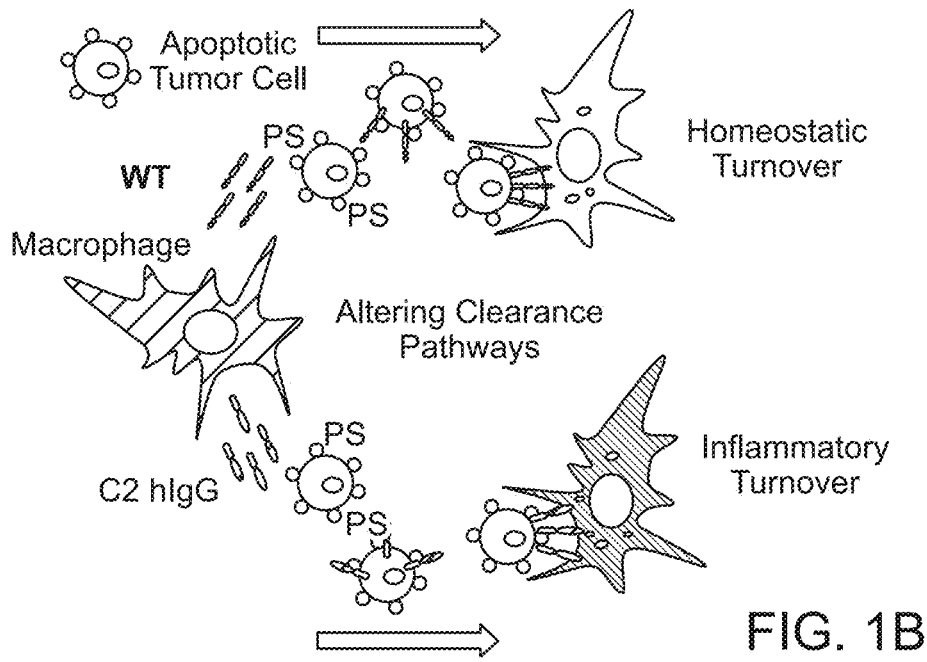
Figure 1C:
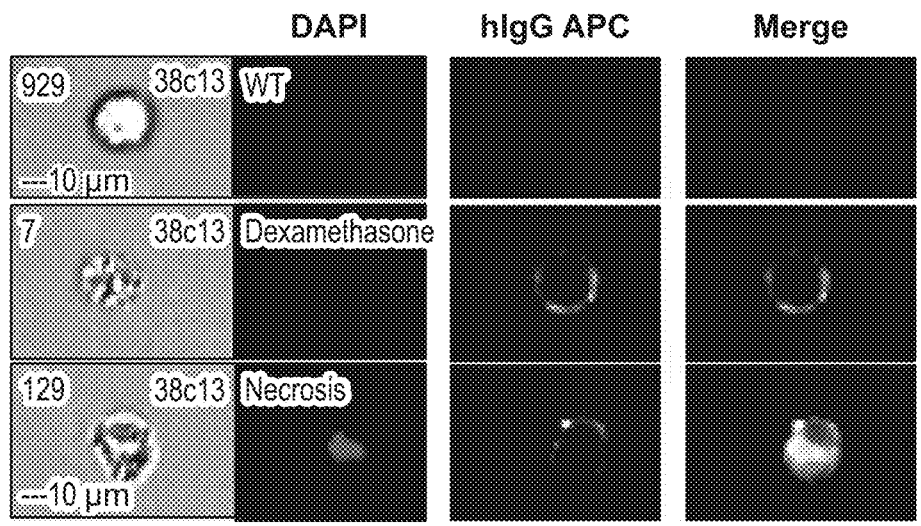
Figure 1D:
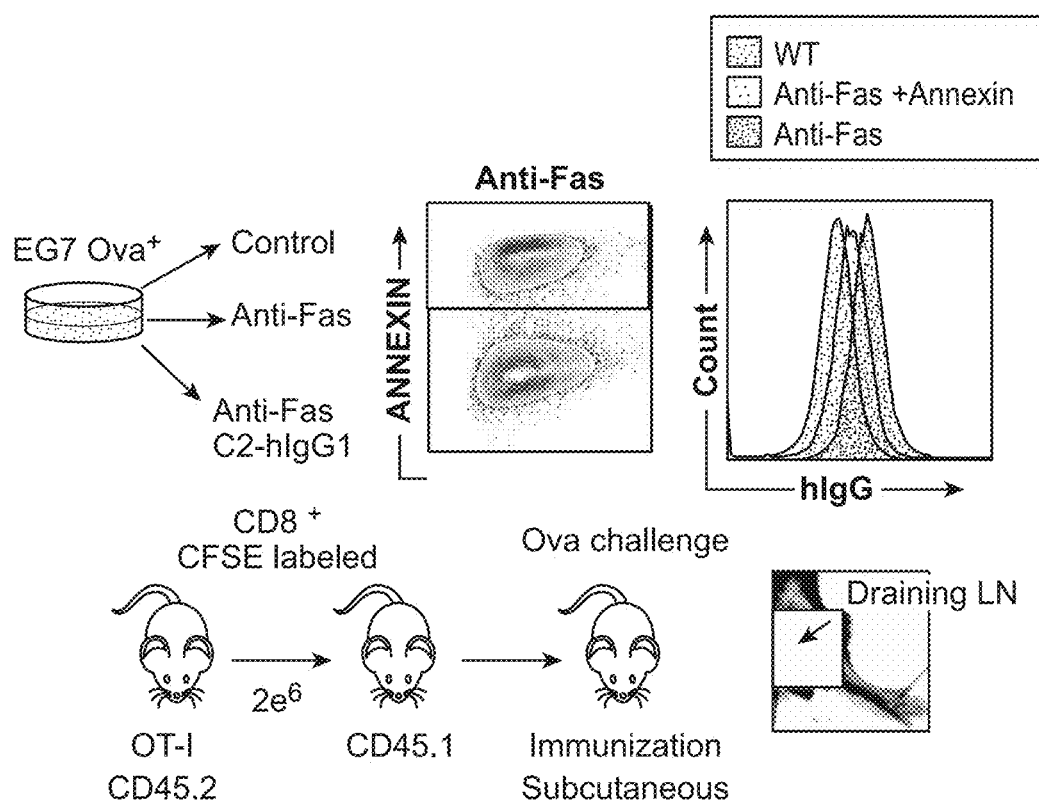
Figure 1E:
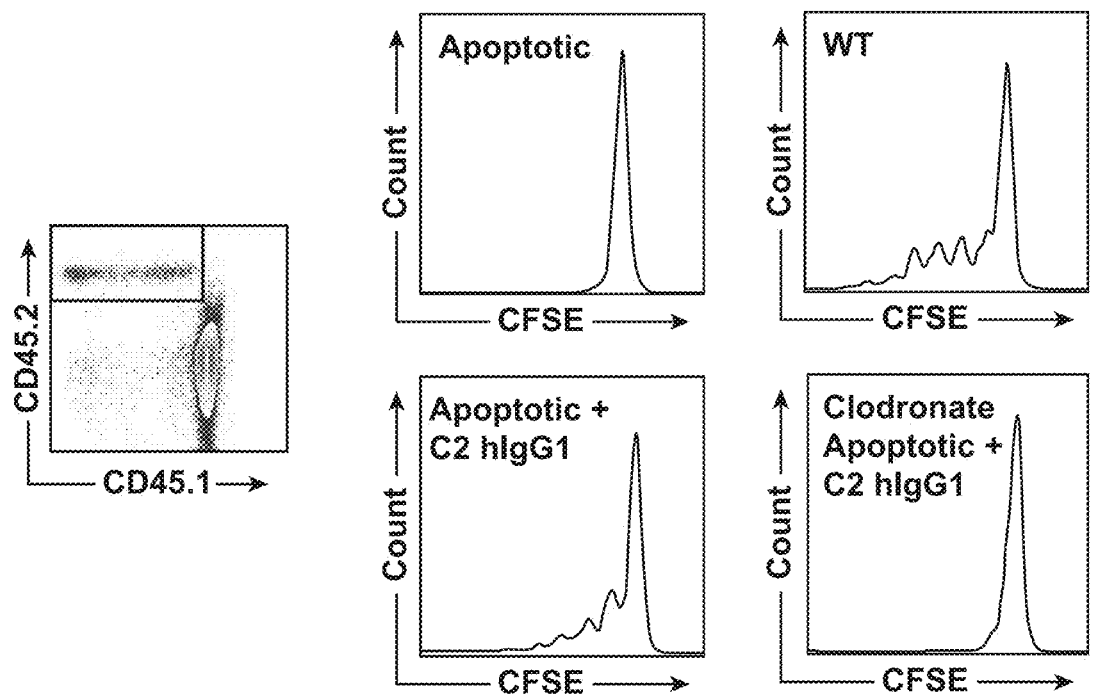

We first sought to examine the capacity of antigen presenting cells (APCs) to cross present dead cell-associated antigens. In these studies, we utilized the OT-I transgenic T cell receptor (TCR) mouse system to measure proliferative $CD8^+$ T cell responses in draining lymph nodes (dLNs) of mice after subcutaneous injection of apoptotic EG7-OVA cells (a T cell lymphoma line expressing ovalbumin). Dead tumor cells are transported via lymphatic flow to dLNs and internalized by tissue resident macrophages for antigen cross-presentation. We first examined OVA-specific $CD8^+$ T cell responses after ex-vivo treatment with anti-FAS antibody (FIG. 1d). Antibody crosslinking of FAS receptor (TNFRSF6) transduces an apoptotic signal leading to cell death on FAS-bearing target cells. After injection of EG7 cells, the number of proliferating and antigen specific $CD8^+$ T increased in dLNs (FIG. 1e). However, we found a decreased presence of these cells in the dLNs of animals injected with EG7 cells treated with anti-Fas antibody (FIG. 1e). These findings are consistent with prior observations showing the immunosuppressive effects of apoptotic cells.

On the basis of these studies, we next examined whether altering mechanisms of clearance of dead tumor cells might fulfill a specific role in establishing antitumor immunity. We derived a PS binding fusion protein by fusing the single 22-kDa PS binding domain of Milk fat globule-EGF factor 8 (MFG-E8) to the Fc fragment of human IgG1 (FA58C2-hIgG1) (FIGS. 1a and 1b). We reasoned that PS blockade through the administration of a synthetically modified PS binding bridge protein might remove inhibitory signals in the homeostatic clearance pathway while simultaneously engaging immune effector cells through the interaction of the IgG Fc domain with Fcγ on phagocytic cells, enhancing immune responses. MFG-E8 is a secreted bridge protein that links PS-exposed membranes through its C2 domain with members of the integrin family of receptors, including $\alpha_v\beta_3$ and $\alpha_v\beta_5$, on macrophages through an Arg-Gly-Asp (RGD) motif. We first assessed the ability of C2-hIgG1 to bind to the surface of PS-exposed apoptotic cells by flow cytometry (FIG. 1c). The binding affinity of C2-hIgG1 increased in a concentration dependent manner up to 0.1 µM, plateauing at higher concentration.

We next examined the effect of C2-hIgG1 on crosspresentation of dead cell-associated antigens. Apoptotic EG7 cells treated ex vivo with anti-FAS antibody were incubated with C2-hIgG1 and injected subcutaneously into wild-type (WT) mice. C2-hIgG1 treatment significantly improved antigen-specific proliferative responses in dLNs (FIG. 1e) compared to apoptotic cells alone. Furthermore, this effect was abolished in macrophage-depleted mice. OT-I T cells were transferred into WT mice, which were then injected subcutaneously with liposomal clodronate. In these mice, liposomal clodronate induced the transient depletion of macrophages in the sinus of dLNs. In the absence of macrophages, immunization with Ova-expressing apoptotic cells incubated with C2-hIgG1 failed to induce OT-I T cell proliferation (FIG. 1e). Taken together, these results show that apoptotic tumor cells, rather than limiting proinflammatory responses, can be induced to elicit inflammatory turnover by altering their clearance in a macrophage-dependent process.

Figure 2A:
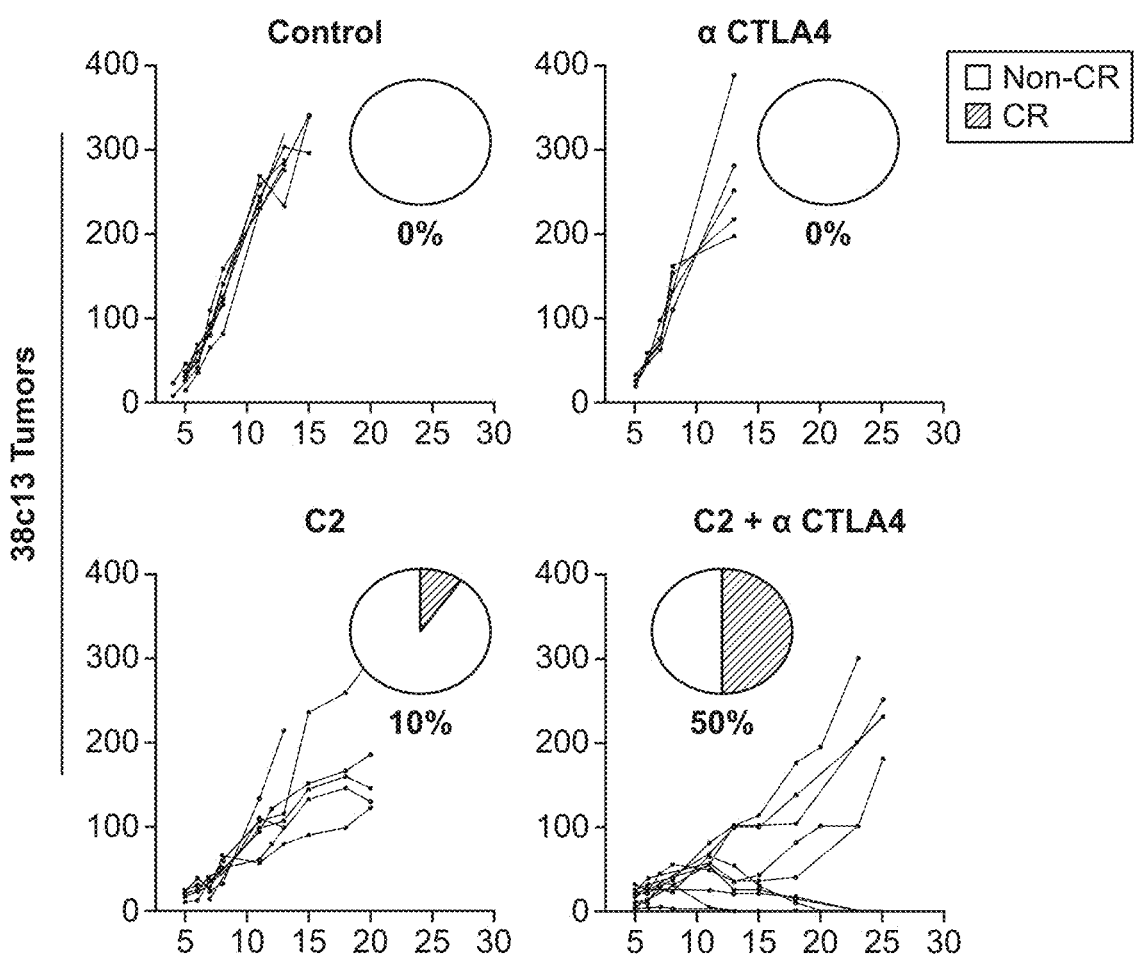
FIG. 2A-2D. Treatment with an anti-phosphatidylserine fusion protein enhances rejection of murine B cell lymphoma cells.
Figure 2B:
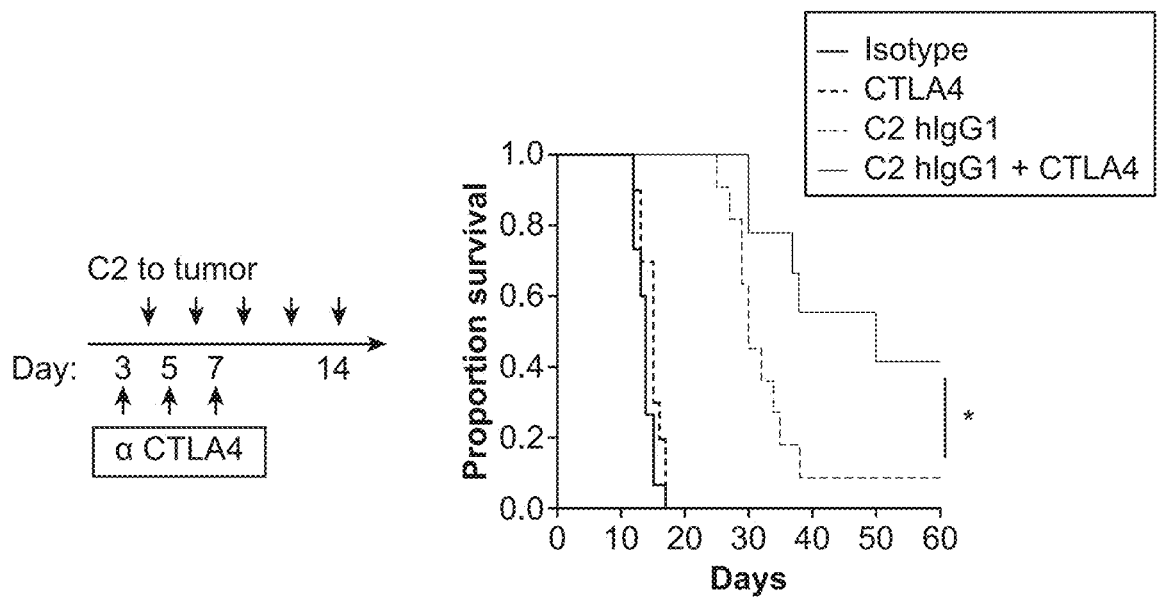

In light of this activation, we next examined whether clearance induced inflammation resulted in enhanced rejection of tumor cells. We injected groups of C3H mice with 38c13 lymphoma cells (38c13). The 38c13 lymphoma line is a highly proliferative, carcinogen-induced B-cell lymphoma of C3H/HeN origin. Two groups were treated with a series of intraperitoneal injections of either C2-hIgG or isotype control (anti-EGFR hIgG1). All mice left untreated developed tumor progression and required euthanasia by 17 days after inoculation. Treatment with C2-hIgG1 reduces the growth of established tumors, but 9 of 10 mice developed progressive disease (FIG. 7). These results were promising and were consistent with our hypothesis. We reasoned that binding of the anti-PS reagent to endogenous PS molecules might be limiting its accumulation within the tumor microenvironment, thereby reducing the anti-tumor therapeutic efficacy. To test for this, we examined the effect of local rather than systemic administration of C2-hIgG1 (FIGS. 2a and 2b). Two groups were treated with a series of injections into the local tumor site (i.t.) of either C2-hIgG1 or isotype control. Intratumoral treatment resulted in significantly reduced tumor growth compared with isotype controls. Furthermore, local treatment appeared to be more effective than systemic therapy.

Figure 3E:
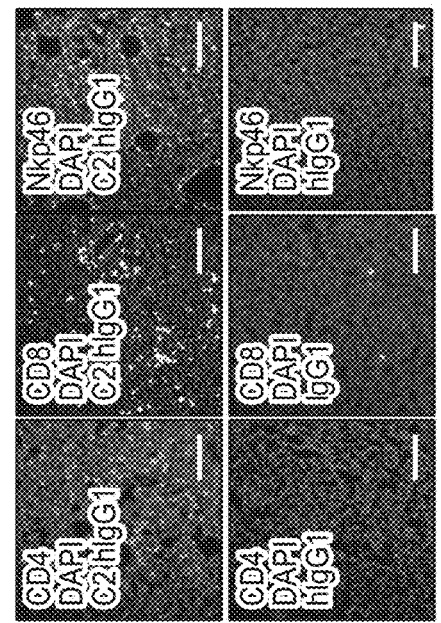
Figure 3G:
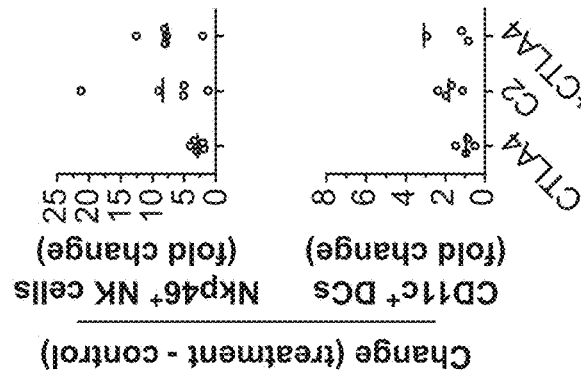
Figure 3D:
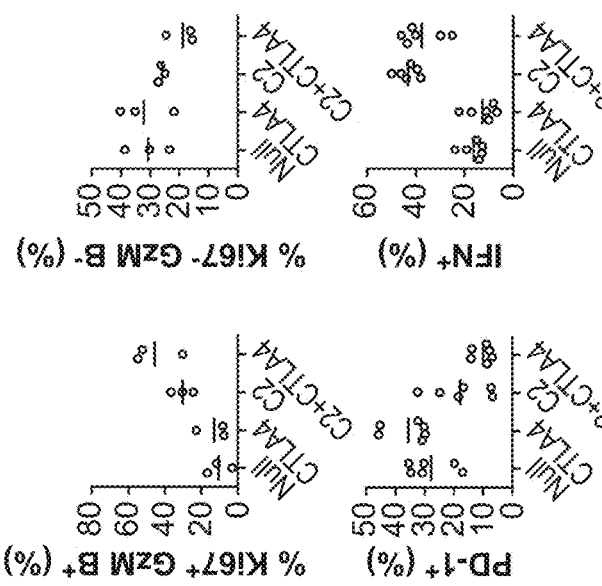
Figure 3F:
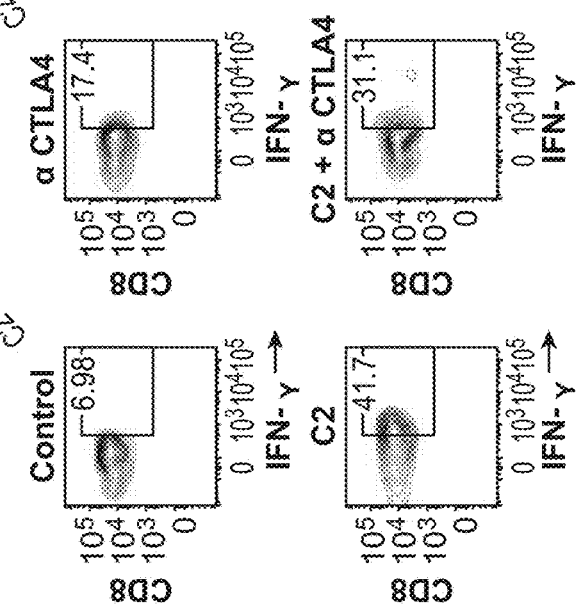

Much as we observed in lymph nodes, we anticipated treatment with C2-hIgG1 might enhance local anti-tumor immune responses. To investigate these effects, we characterized tumor-infiltrating immune cells (TILs) (FIG. 3a-g). The type and density of immune cells within tumors have been implicated in predicting clinical outcomes. In 38c13 tumors, C2-hIgG1 markedly increased the proportion of $CD8^+$ T cells and the proportion that were $Ki67^+$ and $GzmB^+$ within this subset (FIGS. 3c and 3e). C2-hIgG appeared to be a strong driver of intratumoral T-cell proliferation. Intratumoral Treg proliferation was also highest with C2-hIgG but was very similar among all treated and untreated samples (FIG. 3b). In untreated tumors, there was a striking absence of $CD8^+$ TILs that were $Ki67^+$ and $GzmB^+$ (FIG. 3c). Similarly, in C2 treated-tumors, increases in the $CD8^+$ to $T_{reg}$ ratio, proportion of natural killer cells (NK cell), and $CD11c^+$ dendritic cells (DCs) were observed, suggesting enhanced entry and retention of effector cells into the tumor microenvironment.

We next examined the effects of pairing local administration of C2-hIgG1 with an immune checkpoint-blocking agent. Clinical tumor specimens showing higher numbers of pre-existing $CD8^+$ T cells correlate with responses to immune checkpoint blockade, providing a rational for this approach. Furthermore, depletion of $CD4^+$ and $CD8^+$ T cells prior to tumor challenge abolishes the anti-tumor effect of C2-hIgG1 therapy, indicating both of these subsets contribute to tumor eradication in our system (FIG. 7). Combination with the co-inhibitory receptor CTLA-4 is synergistic, resulting in complete responses (CR) in half the animals challenged with 38c13 lymphoma cells (FIG. 2a). The combination of C2-hIgG1+anti-CTLA-4 similarly expands infiltrating T cells and reduces regulatory T and myeloid cells compared to α-CTLA-4 blockade alone (FIG. 3b). A reduction in the fraction of TILs composed of Tregs were observed as well as increases in the numbers of CD8+ T cells, NK, DC, and CD4+ INF+ T cells. In full agreement with these results, subsets of CD8+ T cells display an increased proportion of cells with activation and proliferation markers (FIG. 3, e to h), including expression of PD-1.

Figure 2C:
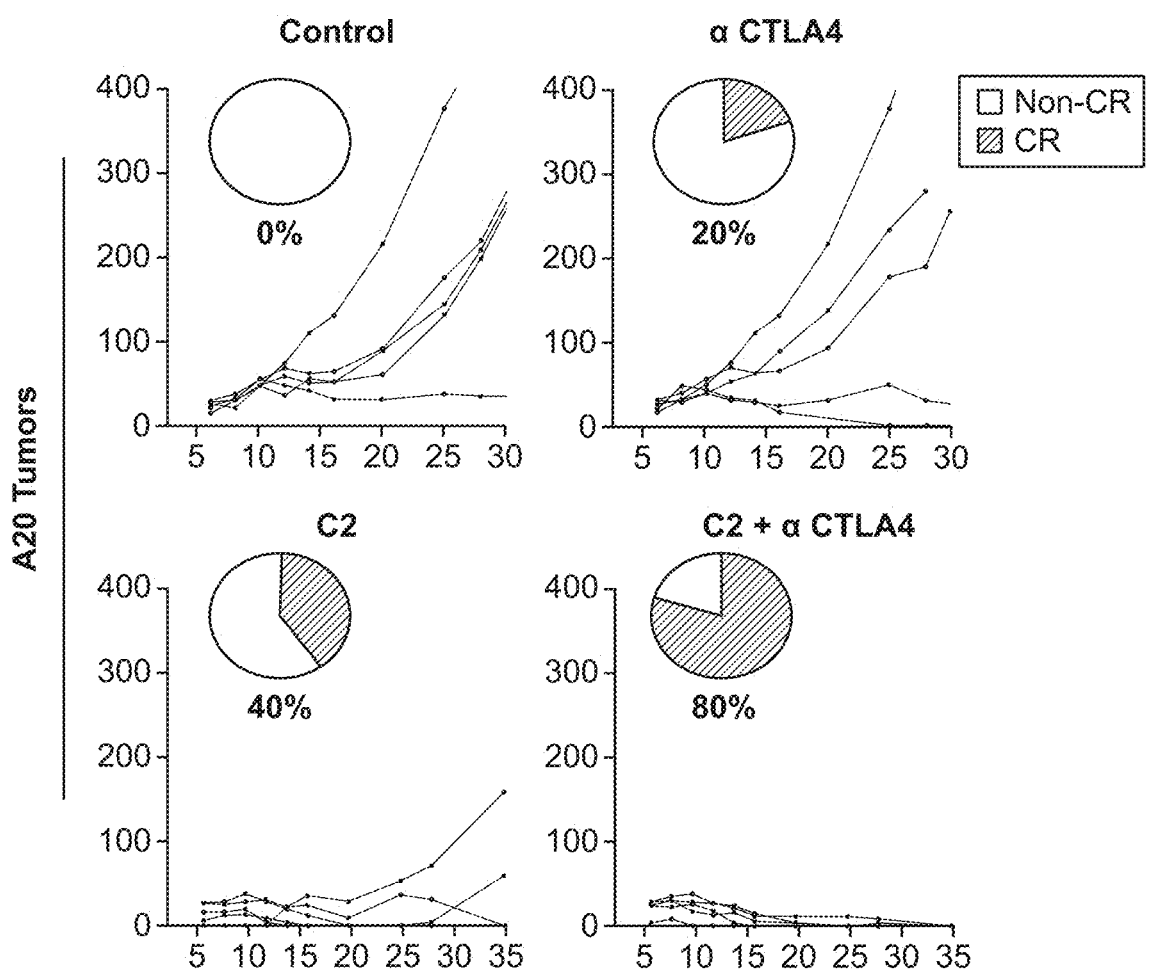
Figure 2D:
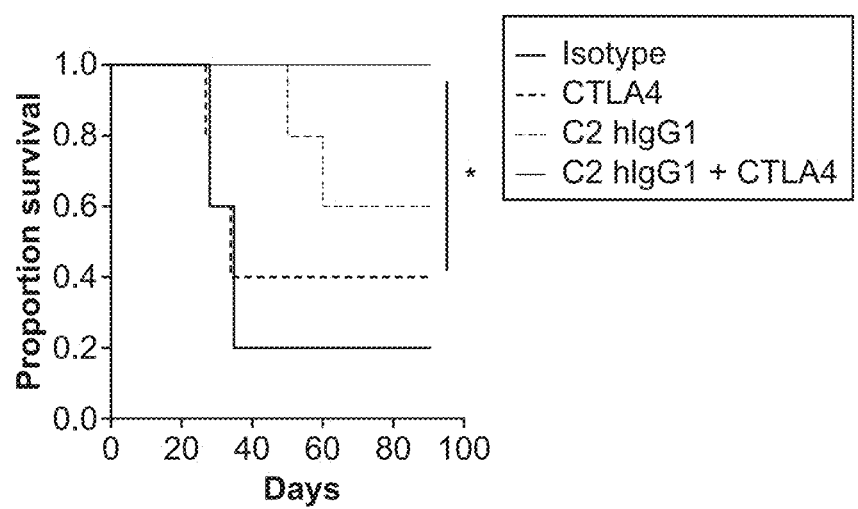

The effects of combination CTLA-4 blockade with C2-hIgG1 were not limited to the murine 38c13 lymphoma line. More substantial survival benefits were obtained with the A20 Balb/c lymphoma cell line. The combination of intra-tumoral administration of C2-hIgG1+anti-CTLA-4 had a dramatic effect on tumor growth, significantly enhancing rejection of A20 challenged recipients (FIG. 2c-d). Mice that had rejected treatment were rechallenged with $1\times10^6$ cells (twice the initial challenge cell number) on day 45. Five naïve mice were also injected as controls (Figure). All control mice developed progressive disease and were euthanized on day 28 after inoculation. Five of five previously immunized mice remained tumor-free 45 days after challenge. These results demonstrate that tumor rejection mediated by C2-hIgG1+anti-CTLA-4 results in induction of immune memory.

The data demonstrate C2-hIgG promotes T cell priming against tumor-associated antigens allowing enhancement of effector cells within the tumor. We further hypothesized inhibitory signals in the homeostatic clearance pathway may limit the effectiveness of adoptive transfer of tumor infiltrating lymphocytes. To test this idea more directly, we examined whether endowing genetically engineered T Cell Receptor (TCR) or chimeric antigen receptor-redirected (CAR T) lymphocytes with an anti-phosphatidylserine bridge protein may permit enhanced function. We initially transduced OT-I T cells with a C2-hIgG1 retroviral vector containing an IL-2 signal leader peptide sequence, to promote protein excretion (FIG. 4a). Examination of recombinant fusion protein in the supernatant of transduced T cells revealed increased expression of C2-hIgG1 compared to untransduced T cells. Protein production was concentration dependent—in the low nanomolar range at concentrations of 500-1000 T cells per ul (FIG. 4b). With an equilibrium constant in the low nanomolar range, we reasoned this concentration of protein would be sufficient to bind to apoptotic cells. To test their functional activity, anti-CD3/CD28 activated OT-I transduced T cells were cocultured with Ova-expressing EG7 cells. The cytolytic activity of the OT-I$^{C2-hIgG1}$ was comparable to that of OT-I$^{WT}$ cells (FIG. 4d). High specific killing activity was maintained, even at a 1:1 effector/target ratio. In parallel, we also observed that target cells in OT-I$^{C2-hIgG1}$ wells were coated with secreted protein (FIG. 4c-f). CTLs kill their targets by ligation of death receptors on the target cell or by granule exocytosis, inducing classic apoptotic cell death.

Figure 5A:
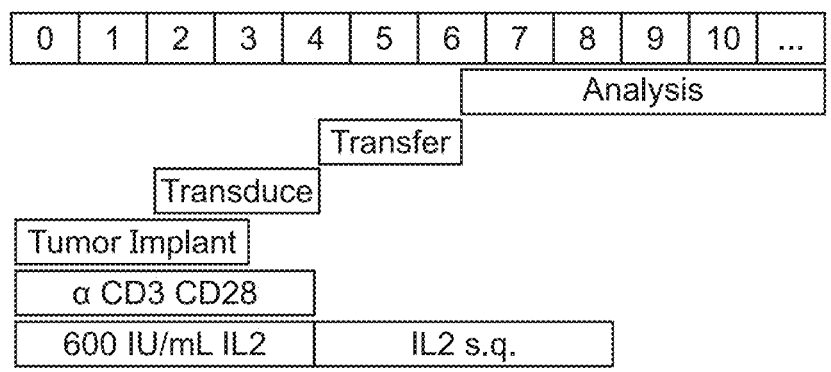
FIG. 5A-5G. In vivo characterization of the anti-tumor effects of a CTL delivered anti-phosphatidylserine fusion protein FIG. 5A, Anti-CD3/CD28 activated OT-I T cells were transduced with retrovirus encoding a secretable anti-phosphatidylserine fusion protein and adoptively transferred into mice bearing ova-expressing EG7 tumors.
Figure 5B:
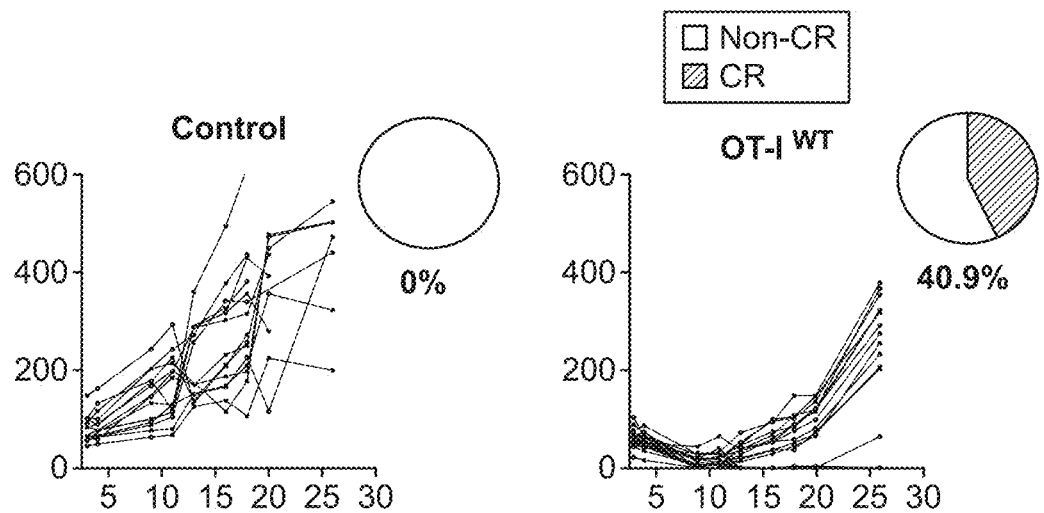
Figure 5B:
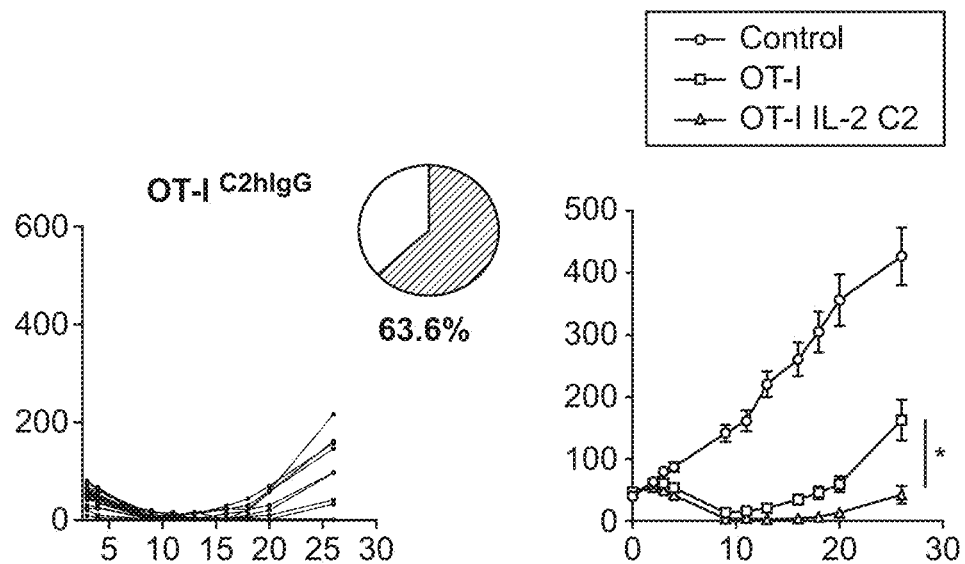
Figure 5C:
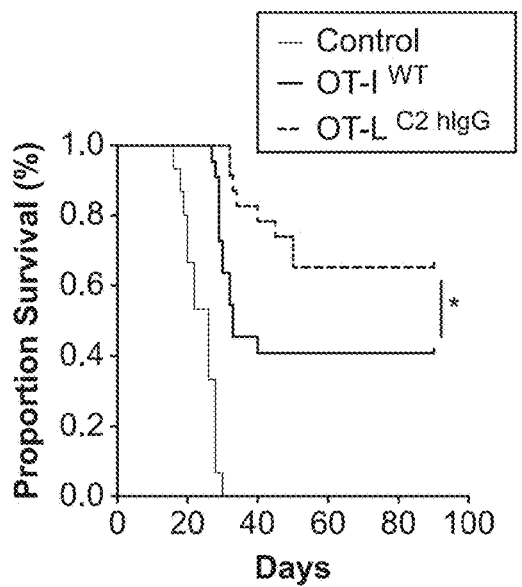
Figure 5D:
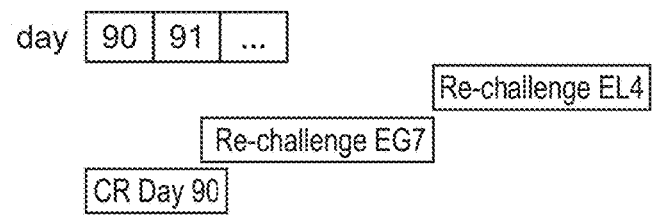
Figure 5E:
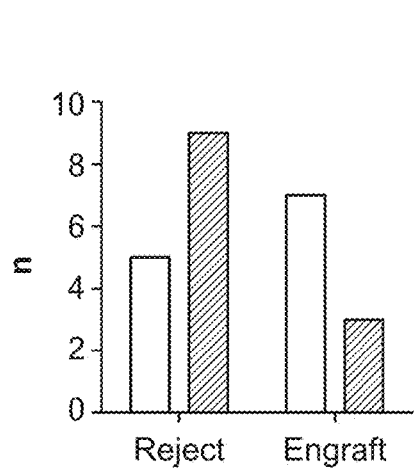
Figure 5F:
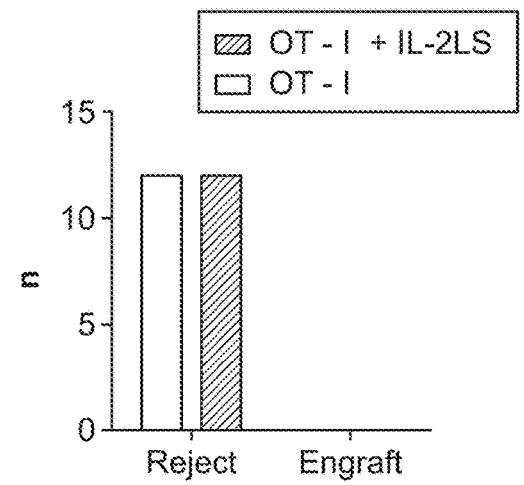
Figure 5G:
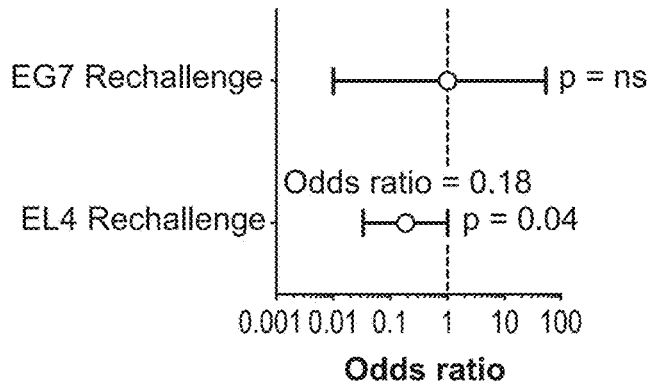

Much as we observed using C2-hIgG, we anticipated cell based delivery to the tumor microenvironment would influence the quality and quantity of the inflammatory response by promoting tumor antigen cross presentation. To measure the functional activity of OT-I$^{C2-hIgG1}$, generated as previously described, $4\times10^6$ OT-I$^{C2-hIgG1}$ were IV injected into wild-type C57BL/6 mice bearing ova-expressing EG7 tumors of 6 mm average diameter (FIG. 5a). Animals received 72 hours of high dose IL-2 following infusion of cells. As expected, EG7 tumors grew rapidly in the control group while animals receiving adoptive transfer of activated OT-I T cells had robust antitumor activity and improved survival. The addition of an engineered C2-hIgG transgene into OT-I T cells results in significantly enhanced (p<0.01) tumor regression and survival (p<0.01) compared with mice given the standard treatment of OT-I T cells (FIG. 5b-c). These animals were later rechallenged on day 90 following tumor inoculation with $1\times10^6$ EG7 cells. In both OT-I$^{WT}$ and OT-I$^{C2-hIgG1}$ groups, previously immunized mice remained tumor-free 60 days after rechallenge (n=14, both groups) (FIG. 5d-f). However, upon evaluation for the potential occurrence of epitope spreading, as might be expected in the OT-I$^{C2-hIgG1}$ group, we observed protective responses to the parental non-Ova expressing EL4 lymphoma. Following rechallenge with transplanted EG7 tumors, mice were challenged with $1\times10^6$ EL4 cells (FIG. 5d-e). Only three of twelve mice developed tumors in OT-I$^{C2-hIgG1}$ mice whereas nine of fourteen mice developed tumors in OT-I$^{WT}$ mice (Odds Ratio=0.185, p=0.04) (FIGS. 5e and 5g). Cellular based delivery of a cross priming agent in the context of antitumor cytotoxic T cell (CTL) responses may promote additional spread of epitopes distinct from target-tissue-inducing epitopes.

Figure 6A:
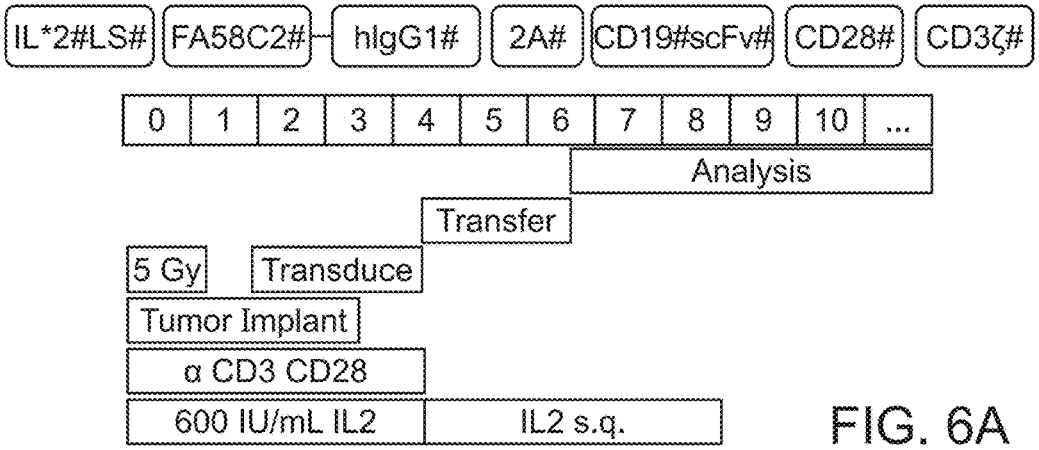
FIG. 6A-6C. Anti-tumor effects of Chimeric Antigen Receptor (CAR T) delivered anti-phosphatidylserine fusion protein.
Figure 6B:
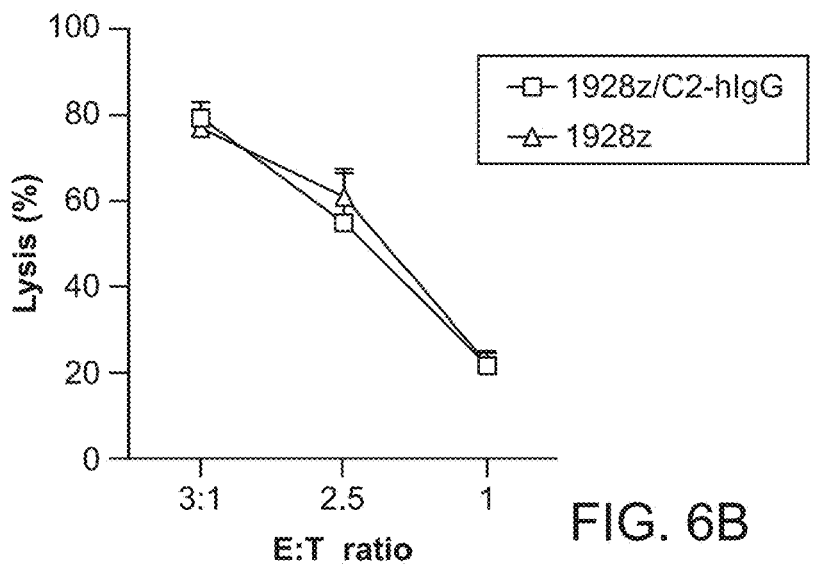
Figure 6C:
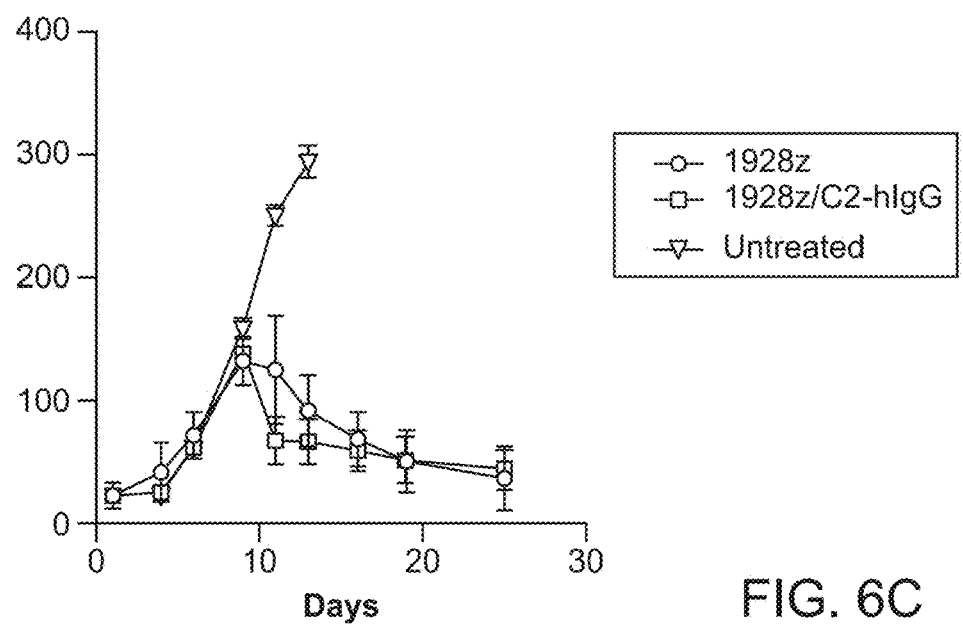
Figure 8:
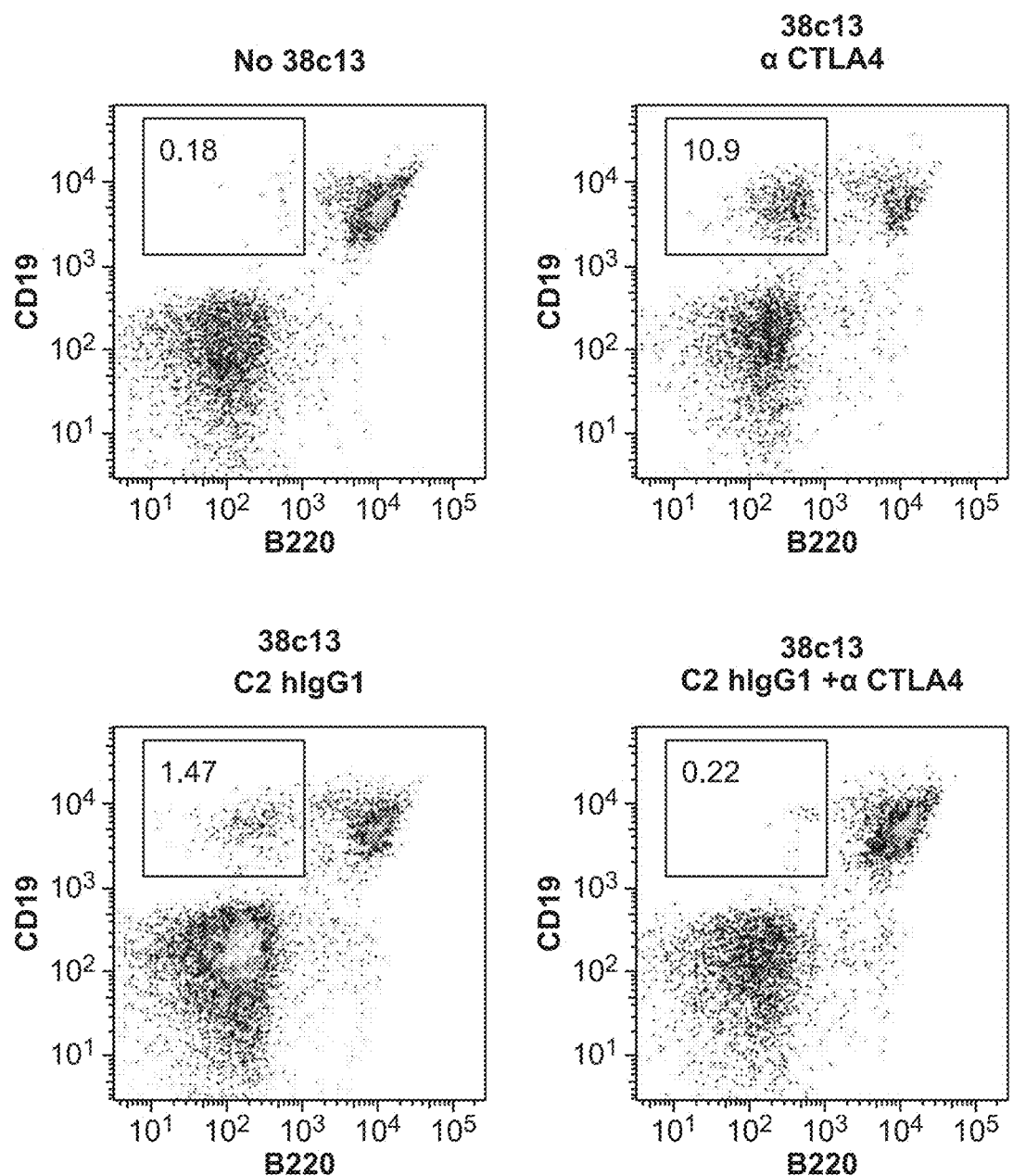
FIG. 8. The combination of C2-hIgG1+α CTLA4 eradicates disseminated lymphoma cells. Day 16 peripheral blood FACS plots showing CD19 and B220 staining. The 38c13 lymphoma line expresses CD19 but not B220. In contrast, normal circulating B cells (top left) do not have a substantial population of CD19$^+$ B220$^-$ cells. 16 days after lymphoma challenge, peripheral blood was stained to detect normal B cells. The numbers on the plots are the percentages of live cells in each quadrant. The combination of C2-HigG1+α CTLA4 eradicates disseminated lymphoma cells (bottom right).

In parallel, we tested whether adoptively transferred chimeric antigen receptor T (CAR T) cells modified to produce an anti-phosphatidylserine bridge protein might enhance anti-tumor responses. Although CAR T cells bypass the requirement for a specific TCR/peptide MHC interaction, it could be that activation of tumor-specific bystander cells further recruit effective antitumor responses. T cells introduced with a bicistronic vector encoding both a CD19-specific CAR (1928z) and C2-hIgG preceded by an IL-2 signal peptide sequence (1928z/C2-hIgG T cells) exhibited similar cytotoxicity in vitro (FIG. 6b) against CD1$^9$ murine cell lines. The murine 1D3 CD19 scFv CAR T has been previously characterized. To investigate the in vivo antitumor activity of 1928z/C2-hIgG T cells, we utilized the syngeneic 38c13 tumor model used in our previous studies. Mice received 5 Gy of total body irradiation (TBI) followed by intravenous injection of $6\times10^6$ CAR-transduced T cells (FIG. 6c). 1928z transduced T cells eradicate established subcutaneous lymphoma masses however we observe no significant enhancement in efficacy in 1928z/C2-hIgG treatment groups (FIG. 6c).

In the present study, we sought to alter immune recognition of apoptotic tumor cells to potentiate antitumor immunity. Engagement of apoptotic cells by phagocytes is well known to elicit production of mediators that actively suppress inflammation in the local tissue milieu. Examples of this occur during periods of development, where large numbers of cells undergo apoptosis and are removed by phagocytes. However, to what degree homeostatic cell turnover programs contributes to immune homeostasis within tumor microenvironments remains an open question.

Molecular bridging between phagocytes and exposed PS on apoptotic cells is a conserved mechanism for the clearance of cell corpses. We utilized a molecular bridge scaffold to engineer a modified phosphatidylserine bridge protein that works as a bridge between apoptotic cells expressing aminophospholipids and phagocytes bearing Fc receptors. We anticipated this approach would convert 'quiet clearance' of dying tumor cells into a pro-inflammatory event. The rational for this approach can be found in patients with persistent and relapsing inflammatory disorders such as anti-phospholipid antibody syndrome. Such autoantibodies opsonize apoptotic cells substantially enhancing recognition and binding by scavenger macrophages, with the result that TNF is massively promoted rather than suppressed.

Our results indicate that altering clearance of dying cancer cells to elicit inflammatory turnover can allow for and potentiate immune responses against tumor cells. Despite significant progress, many conventional immune strategies have had limited effect on patient survival, suggesting that combination therapy to simultaneously target multiple forms of immune suppression may be necessary. When combined with immune checkpoint inhibitors, the addition of a modified PS binding bridge protein significantly enhances their efficacy. The mechanisms by which this is occurring may be complex; we show enhancement of crosspresentation of tumor cell antigens and licensing of the tumor microenvironment via recruitment and retention of inflammatory effector cells.

The effects of anti-PS bridge therapy as an immune adjunct were not limited to antibody-based therapies. As naturally occurring secreted molecules, these agents lend themselves well to a cellular based delivery platform. It has been well characterized that maximizing T cell activity may require both overcoming inhibitory programs downstream of T cell signaling as well as micro environmental barriers that are independent of TCR specificity. The addition of C2-hIgG transgene to engineered TCRs significantly enhances tumor regression and survival compared to standard treatment. This approach utilizes CTLs that both induce apoptosis upon target cell recognition and simultaneously export anti-PS bridge protein to opsonize cells. That such an approach enhances adoptive TCR based therapies and promotes additional spread of epitopes underscores the potential for target cell death to influence the magnitude of downstream inflammatory responses by modulating antigen processing and presentation. A TCR-based therapy coupled to anti-PS bridge proteins may have an advantage through recognition of antigen/MHC complexes and costimulatory ligands.

Thus, anti-PS bridge therapy, by removing inhibitory signals in the homeostatic clearance pathway, provides a useful adjunct to other therapeutic approaches involving immune checkpoint therapy or engineered TCRs.

Materials and Methods

Cloning and Expression of Fusion Proteins.

FA58C2-Fc fusion proteins were produced by cloning the FA58C2 domain, residues 227-335, from hMFG-E8 into the pFUSE-hIgG1-Fc vector (Invivogen) with an IL-2 secretion tag. The FA58C2 domain and Fc fragment were joined together by a $(Gly_4Ser)$ linker. Proteins were expressed by transient transfection in Freestyle 293-F cells (Invitrogen) and purified over HiTrap Protein A columns (GE Healthcare). Elutions were equilibrated in 1xPBS buffer and concentrated to 1 mg/mL and stored at $-80°$ C. LPS content was tested using the LAL Chromogenic Endotoxin Quantification Kit (Pierce) according to the manufacturer's instructions.

In Vivo Proliferation of OT-I Cells.

Ova-specific OT-I $CD8^+$ T cells from spleens were enriched by immunomagnetic isolation. Cells were labeled with 2 μM CFSE and $4\times10^6$ cells were injected intravenously into CD45.1 wild-type C57BL/6 mice on day $-1$. Then, $1\times10^7$ EG7 cells were treated with anti-CD95 (clone Jo2) for 8 hr, washed in HBSSx2, and injected subcutaneously into the hindlimb footpads of mice. Draining popliteal LNs were resected on day 3 (72 hr after the injection). CFSE fluorescence intensity was analyzed by FACS. In some experiments, Ova-expressing apoptotic cells were incubated with FA58C2-Fc fusion proteins or HBSS for 30 minutes, washed in HBSSx2, and then injected subcutaneously into footpads. To deplete popliteal LN macrophages, 25 ul of liposomal clodronate was injected into the footpads of mice on day $-5$ and day-4 prior to adoptive transfer of OT-I T cells.

Tumor Transplantations.

38c13 cells were a gift from Ron Levy (Stanford University). We used C3H/HeN-MTV-negative mice (Charles Rivers) for all 38c13 experiments. The EG7 and EL4 cells were purchased from ATCC and engrafted into C57BL/6J mice. For in vivo challenge experiments $0.5\times10^5$ cells were inoculated by s.c. injection in 200 ul of Hanks balanced salt solution (HBSS). Tumor size was measured in two dimensions using precision calipers and significance was determined using Mann-Whitney test with Bonferroni correction for the indicated comparisons. Mice were euthanized when the total tumor size exceeded 2 $cm^2$. For rechallenge experiments, animals were injected subcutaneously with $1\times10^6$ tumor cells.

Tumor Immunotherapy.

Anti-CTLA-4 antibody (200 μg each) was administered by i.p injection in 200 μl PBS on days two, four, and seven after tumor inoculation, according to prior publications. Therapy was started usually around day 5 after tumor inoculation. C2-hIgG1 was injected i.t. into a single tumor at a dose of 50 μg daily for days 1-7, 9, 11, and 13 or given systemically (200 μg each) by i.p injection in 200 μl PBS according to the same dosing schedule.

CD4, CD8 T Cell and NK Cell Depletions.

Anti-CD8, anti-CD4 depleting mAbs (clone 2.43 and GK1.5, respectively), and asialo GM1 (Wako Chemicals) were used to deplete CD4, CD8, and NK cells. Depleting antibodies were injected i.p. on day $-1$ and day 0 of tumor inoculation, and every 5 days thereafter at dose of 250 μg per injection of anti-CD4 mAb or anti-CD8 mAb and 50 μl per injection of anti-asialo GM1.

Flow Cytometry and Mouse Blood Cell Immunophenotyping.

For FACS analysis of in vivo experiments, tumor and dLNs were harvested at day 10 post-tumor implantation. Single-cell suspensions were prepared and red blood cells were lysed using ACK lysis buffer. For intracellular staining, cells were fixed in 2% paraformaldehyde for 5 minutes (after cell surface staining in PBS with 2% FBS FACS buffer), washed with PBSx2, and then permeablized in Saponin 0.1% in PBS with 2% FBS for 15 mins. Following permeabilization, cells were stained with directly conjugated antibodies for 30 minutes, washed, and analyzed by FACS. T effector cells were classified as $CD8^+$ $CD44^+$, myeloid derived suppressor cells as $CD11b^+GR-1^+$, NK cells as $CD3^-$ $NKp46^+$, and regulatory T cells as $CD4^+$ $FoxP3^+$.

Sub Cloning and Vector Construction.

To augment secretion of protein in vivo we utilized the peptide leader sequence from IL-2 MYRMQLLSCIALSLA-LVTNS. IL-2 signal peptide was inserted upstream of the FA58C2-Fc protein coding sequence and cloned into the retroviral backbone MSGV by site-overlap extension (SOE). A gene block fragment containing the chimeric antigen receptor (1928z) was joined together with IL2 FA58C2-Fc by a 2A self-cleaving sequence and the fragment was then inserted into the retroviral vector MSGV (1928z/C2-hIgG).

In Vitro Activation of Murine T Cells and T Cell Transduction.

To produce retroviral supernatant, stocks were prepared by transient transfection of retroviral plasmid of 293 Phoenix-Eco packaging cells following a standard calcium precipitation protocol. RBC lysed murine splenocytes were cultured in RPMI supplemented with 10% heat-inactivated FBS, 50 μM β-mercapto-ethanol and 600 IU/mL of rhIL-2 with anti-CD3 coated plates and anti-CD28 containing media. At 48 h postactivation, cells underwent a single round of spinfection with retrovirus supernatant at 2500 rpm, 120 mins, $32°$ C.

Adoptive T Cell Transfer Experiments.

C57BL/6 mice implanted with EG7 or EL4 tumors were randomized into OT-I$^{C2-hIgG1}$ or OT-I$^{WT}$ treatment groups. 24 hours after spinfection, T cells were washed with HBSS and used in cell transfer experiments. 4×10$^6$ OT-I T cells were injected IV into recipients. The average diameter of EG7 tumors at the time of transfer was 6 mm. Recombinant human IL-2 (5 ug) was injected intraperitoneally on days 0, 1, and 2. For CAR-T cell experiments, C3H/HeN-MTV-negative mice received 5 Gy of TBI followed by injection of 0.5×10$^6$ 38c13 cells. Four days later, mice were randomized to 1928z/C2-hIgG or 1928z T cells and infused with 6×10$^6$ CAR transduced T cells. Recombinant human IL-2 (5 ug) was injected intraperitoneally on days 0, 1, and 2. For in vitro characterization of retroviral-transduced supernatants, human IgG was quantified in a sandwich ELISA according to the manufacturer's instructions (ebioscience cat #88-50550).

Statistical Analysis.

Differences between the means of experimental groups were analyzed with a two-tailed Student's t test or ANOVA (Prism GraphPad software). Bonferroni multiple comparison test was used following two-way ANOVA. p values % 0.05 were considered significant.

Sequences (SEQ ID NO:1), MFG-E8 hIgG1. Residue 1-20 comprise a secretion tag; residues 21-181 comprise the FA5AC2 domain of MFG-E8, residues 182-186 are a linker; and 187-413 comprises a human IgG1 Fc domain.

MYRMQLLSCIALSLALVTNSLNGCANPLGLKNNSIPDKQITASSSYKTWG

LHLFSWNPSYARLDKQGNFNAWVAGSYGNDQWLQVDLGSSKEVTGIITQG

ARNFGSVQFVASYKVAYSNDSANWTEYQDPRTGSSKIFPGNWDNHSHKKN

LFETPILARYVRILPVAWHNRIALRLELLGCGGGSDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHN

HYTQKSLSLSPGK*

(SEQ ID NO:2), Tim-4 hIgG1. Residue 1-20 comprise a secretion tag; residues 21-154 comprise the human TIM4 PS domain, residues 155-159 are a linker; and 160-386 comprises a human IgG1 Fc domain.

MYRMQLLSCIALSLALVTNSTSETVVTEVLGHRVTLPCLYSSWSHNSNSM

CWGKDQCPYSGCKEALIRTDGMRVTSRKSAKYRLQGTIPRGDVSLTILNP

SESDSGVYCCRIEVPGWFNDVKINVRLNLQRASTTTDEKFNLKLVIKPAK

VTPAGGGGSDKTHTCPPCPAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLT

VDKSRWQQGNVFSCSVMHEALHNHYTQKSLSLSPGK*

(SEQ ID NO:3), Tim-1 hIgG1. Residue 1-20 comprise a secretion tag; residues 21-134 comprise the human TIM1 PS domain, residues 155-159 are a linker; and 160-386 comprises a human IgG1 Fc domain.

MYRMQLLSCIALSLALVTNSAGSVKVGGEAGPSVTLPCHYSGAVTSMCWN

RGSCSLFTCQNGIVWTNGTHVTYRKDTRYKLLGDLSRRDVSLTIENTAVS

DSGVYCCRVEHRGWFNDMKITVSLEIVPPKVTTDGGGGSDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK*

What is claimed is:

1. A method of enhancing immune responsiveness in an individual toward a targeted cancer cell population comprising apoptotic cells, the method comprising:
   administering a cell, comprising a polynucleotide encoding a phosphatidylserine tether protein, comprising: (i) a phosphatidylserine (PS) binding domain of a TIM family protein or MFG-E8 joined to (ii) an immunomodulatory receptor present on an antigen presenting cell, in a dose effective to increase immune responsiveness to the targeted cell population.

2. The method of claim 1, wherein the targeted cell population is a cancer cell population.

3. The method of claim 1, further comprising administering a second therapy to increases apoptosis of the targeted cell population.

4. The method of claim 1, further comprising administering a second therapy to increase immune responsiveness.

5. The method of claim 4, wherein the second therapy comprises administration of an immune checkpoint inhibitor.

6. The method of claim 4, wherein the second therapy comprises administration of a tumor: specific antibody.

7. The method of claim 4, wherein the second therapy comprises administration of an immune costimulatory molecule agonist.

8. A method of enhancing immune responsiveness in an individual toward a targeted cancer cell population comprising apoptotic cells, the method comprising:
   administering a cell, comprising a polynucleotide encoding a phosphatidylserine tether protein, comprising: ((i) a phosphatidylserine (PS) binding domain of Tim-4, Tim-1, or MFG-E8 joined to (ii) an Fc region of a human immunoglobulin, in a dose effective to increase immune responsiveness to the targeted cell population.

9. The method of claim 8, wherein the Fc region is the Fc region of human IgG1.

10. The method of claim 8, wherein the phosphatidylserine (PS) binding domain and Fc region are joined by a polypeptide linker.

11. The method of claim 8, wherein the protein has a sequence of SEQ ID NO:1, 2 or 3.

* * * * *

SEQUENCE LISTING

```
<160> NUMBER OF SEQ ID NOS: 12

<210> SEQ ID NO 1
<211> LENGTH: 413
<212> TYPE: PRT
<213> ORGANISM: Artificial sequence
<220> FEATURE:
<223> OTHER INFORMATION: synthetic polypeptide

<400> SEQUENCE: 1

Met Tyr Arg Met Gln Leu Leu Ser Cys Ile Ala Leu Ser Leu Ala Leu
1               5                   10                  15

Val Thr Asn Ser Leu Asn Gly Cys Ala Asn Pro Leu Gly Leu Lys Asn
            20                  25                  30

Asn Ser Ile Pro Asp Lys Gln Ile Thr Ala Ser Ser Ser Tyr Lys Thr
        35                  40                  45

Trp Gly Leu His Leu Phe Ser Trp Asn Pro Ser Tyr Ala Arg Leu Asp
    50                  55                  60

Lys Gln Gly Asn Phe Asn Ala Trp Val Ala Gly Ser Tyr Gly Asn Asp
```

65                  70                  75                  80
        Gln Trp Leu Gln Val Asp Leu Gly Ser Ser Lys Glu Val Thr Gly Ile
                        85                  90                  95

Ile Thr Gln Gly Ala Arg Asn Phe Gly Ser Val Gln Phe Val Ala Ser
                    100                 105                 110

Tyr Lys Val Ala Tyr Ser Asn Asp Ser Ala Asn Trp Thr Glu Tyr Gln
                    115                 120                 125

Asp Pro Arg Thr Gly Ser Ser Lys Ile Phe Pro Gly Asn Trp Asp Asn
                130                 135                 140

His Ser His Lys Lys Asn Leu Phe Glu Thr Pro Ile Leu Ala Arg Tyr
        145                 150                 155                 160

Val Arg Ile Leu Pro Val Ala Trp His Asn Arg Ile Ala Leu Arg Leu
                        165                 170                 175

Glu Leu Leu Gly Cys Gly Gly Gly Ser Asp Lys Thr His Thr Cys
                    180                 185                 190

Pro Pro Cys Pro Ala Pro Glu Leu Leu Gly Gly Pro Ser Val Phe Leu
                    195                 200                 205

Phe Pro Pro Lys Pro Lys Asp Thr Leu Met Ile Ser Arg Thr Pro Glu
                210                 215                 220

Val Thr Cys Val Val Val Asp Val Ser His Glu Asp Pro Glu Val Lys
        225                 230                 235                 240

Phe Asn Trp Tyr Val Asp Gly Val Glu Val His Asn Ala Lys Thr Lys
                        245                 250                 255

Pro Arg Glu Glu Gln Tyr Asn Ser Thr Tyr Arg Val Val Ser Val Leu
                    260                 265                 270

Thr Val Leu His Gln Asp Trp Leu Asn Gly Lys Glu Tyr Lys Cys Lys
                    275                 280                 285

Val Ser Asn Lys Ala Leu Pro Ala Pro Ile Glu Lys Thr Ile Ser Lys
                290                 295                 300

Ala Lys Gly Gln Pro Arg Glu Pro Gln Val Tyr Thr Leu Pro Pro Ser
        305                 310                 315                 320

Arg Glu Glu Met Thr Lys Asn Gln Val Ser Leu Thr Cys Leu Val Lys
                        325                 330                 335

Gly Phe Tyr Pro Ser Asp Ile Ala Val Glu Trp Glu Ser Asn Gly Gln
                    340                 345                 350

Pro Glu Asn Asn Tyr Lys Thr Thr Pro Pro Val Leu Asp Ser Asp Gly
                    355                 360                 365

Ser Phe Phe Leu Tyr Ser Lys Leu Thr Val Asp Lys Ser Arg Trp Gln
                370                 375                 380

Gln Gly Asn Val Phe Ser Cys Ser Val Met His Glu Ala Leu His Asn
        385                 390                 395                 400

His Tyr Thr Gln Lys Ser Leu Ser Leu Ser Pro Gly Lys
                        405                 410

<210> SEQ ID NO 2
<211> LENGTH: 386
<212> TYPE: PRT
<213> ORGANISM: Artificial sequence
<220> FEATURE:
<223> OTHER INFORMATION: synthetic polypeptide

<400> SEQUENCE: 2

Met Tyr Arg Met Gln Leu Leu Ser Cys Ile Ala Leu Ser Leu Ala Leu
1               5                   10                  15

Val Thr Asn Ser Thr Ser Glu Thr Val Val Thr Glu Val Leu Gly His

```
            20                  25                  30
Arg Val Thr Leu Pro Cys Leu Tyr Ser Ser Trp Ser His Asn Ser Asn
         35                  40                  45

Ser Met Cys Trp Gly Lys Asp Gln Cys Pro Tyr Ser Gly Cys Lys Glu
 50                  55                  60

Ala Leu Ile Arg Thr Asp Gly Met Arg Val Thr Ser Arg Lys Ser Ala
 65                  70                  75                  80

Lys Tyr Arg Leu Gln Gly Thr Ile Pro Arg Gly Asp Val Ser Leu Thr
                 85                  90                  95

Ile Leu Asn Pro Ser Glu Ser Asp Ser Gly Val Tyr Cys Cys Arg Ile
             100                 105                 110

Glu Val Pro Gly Trp Phe Asn Asp Val Lys Ile Asn Val Arg Leu Asn
         115                 120                 125

Leu Gln Arg Ala Ser Thr Thr Thr Asp Glu Lys Phe Asn Leu Lys Leu
     130                 135                 140

Val Ile Lys Pro Ala Lys Val Thr Pro Ala Gly Gly Gly Ser Asp
145                 150                 155                 160

Lys Thr His Thr Cys Pro Pro Cys Pro Ala Pro Glu Leu Leu Gly Gly
                 165                 170                 175

Pro Ser Val Phe Leu Phe Pro Pro Lys Pro Lys Asp Thr Leu Met Ile
             180                 185                 190

Ser Arg Thr Pro Glu Val Thr Cys Val Val Val Asp Val Ser His Glu
         195                 200                 205

Asp Pro Glu Val Lys Phe Asn Trp Tyr Val Asp Gly Val Glu Val His
     210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                 245                 250                 255

Glu Tyr Lys Cys Lys Val Ser Asn Lys Ala Leu Pro Ala Pro Ile Glu
             260                 265                 270

Lys Thr Ile Ser Lys Ala Lys Gly Gln Pro Arg Glu Pro Gln Val Tyr
         275                 280                 285

Thr Leu Pro Pro Ser Arg Glu Glu Met Thr Lys Asn Gln Val Ser Leu
     290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                 325                 330                 335

Leu Asp Ser Asp Gly Ser Phe Phe Leu Tyr Ser Lys Leu Thr Val Asp
             340                 345                 350

Lys Ser Arg Trp Gln Gln Gly Asn Val Phe Ser Cys Ser Val Met His
         355                 360                 365

Glu Ala Leu His Asn His Tyr Thr Gln Lys Ser Leu Ser Leu Ser Pro
     370                 375                 380

Gly Lys
385

<210> SEQ ID NO 3
<211> LENGTH: 366
<212> TYPE: PRT
<213> ORGANISM: Artificial sequence
<220> FEATURE:
<223> OTHER INFORMATION: synthetic polypeptide
```

<400> SEQUENCE: 3

```
Met Tyr Arg Met Gln Leu Leu Ser Cys Ile Ala Leu Ser Leu Ala Leu
1               5                   10                  15

Val Thr Asn Ser Ala Gly Ser Val Lys Val Gly Gly Glu Ala Gly Pro
            20                  25                  30

Ser Val Thr Leu Pro Cys His Tyr Ser Gly Ala Val Thr Ser Met Cys
        35                  40                  45

Trp Asn Arg Gly Ser Cys Ser Leu Phe Thr Cys Gln Asn Gly Ile Val
50                  55                  60

Trp Thr Asn Gly Thr His Val Thr Tyr Arg Lys Asp Thr Arg Tyr Lys
65                  70                  75                  80

Leu Leu Gly Asp Leu Ser Arg Arg Asp Val Ser Leu Thr Ile Glu Asn
                85                  90                  95

Thr Ala Val Ser Asp Ser Gly Val Tyr Cys Cys Arg Val Glu His Arg
            100                 105                 110

Gly Trp Phe Asn Asp Met Lys Ile Thr Val Ser Leu Glu Ile Val Pro
        115                 120                 125

Pro Lys Val Thr Thr Asp Gly Gly Gly Ser Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365
```

<210> SEQ ID NO 4
<211> LENGTH: 5
<212> TYPE: PRT
<213> ORGANISM: Artificial sequence
<220> FEATURE:
<223> OTHER INFORMATION: synthetic polypeptide
<220> FEATURE:

```
<221> NAME/KEY: MISC_FEATURE
<222> LOCATION: (1)..(5)
<223> OTHER INFORMATION: Amino acids at positions 1 to 5 may be repeated
      one, two, three, four, five, six, seven, eight, nine, ten, or
      greater than ten times

<400> SEQUENCE: 4

Gly Ser Gly Gly Ser
1               5

<210> SEQ ID NO 5
<211> LENGTH: 6
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(6)
<223> OTHER INFORMATION: Amino acids at positions 1 to 6 may be repeated
      one, two, three, four, five, six, seven, eight, nine, ten, or
      greater than ten times.

<400> SEQUENCE: 5

Gly Gly Ser Gly Gly Ser
1               5

<210> SEQ ID NO 6
<211> LENGTH: 4
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(4)
<223> OTHER INFORMATION: Amino acids at positions 1 to 4 may be repeated
      one, two, three, four, five, six, seven, eight, nine, ten, or
      greater than ten times.

<400> SEQUENCE: 6

Gly Gly Gly Ser
1

<210> SEQ ID NO 7
<211> LENGTH: 4
<212> TYPE: PRT
<213> ORGANISM: Artificial sequence
<220> FEATURE:
<223> OTHER INFORMATION: synthetic polypeptide

<400> SEQUENCE: 7

Gly Gly Ser Gly
1

<210> SEQ ID NO 8
<211> LENGTH: 5
<213> ORGANISM: Artificial sequence
<220> FEATURE:
<223> OTHER INFORMATION: synthetic polypeptide

<400> SEQUENCE: 8

Gly Gly Ser Gly Gly
1               5

<210> SEQ ID NO 9
<211> LENGTH: 5
<212> TYPE: PRT
```

```
<213> ORGANISM: Artificial sequence
<220> FEATURE:
<223> OTHER INFORMATION: synthetic polypeptide

<400> SEQUENCE: 9

Gly Ser Gly Ser Gly
1               5

<210> SEQ ID NO 10
<211> LENGTH: 5
<212> TYPE: PRT
<213> ORGANISM: Artificial sequence
<220> FEATURE:
<223> OTHER INFORMATION: synthetic polypeptide

<400> SEQUENCE: 10

Gly Ser Gly Gly Gly
1               5

<210> SEQ ID NO 11
<211> LENGTH: 5
<212> TYPE: PRT
<213> ORGANISM: Artificial sequence
<220> FEATURE:
<223> OTHER INFORMATION: synthetic polypeptide

<400> SEQUENCE: 11

Gly Gly Gly Ser Gly
1               5

<210> SEQ ID NO 12
<211> LENGTH: 5
<212> TYPE: PRT
<213> ORGANISM: Artificial sequence
<220> FEATURE:
<223> OTHER INFORMATION: synthetic polypeptide

<400> SEQUENCE: 12

Gly Ser Ser Ser Gly
1               5
```